US009408618B2

(12) United States Patent
Park et al.

(10) Patent No.: US 9,408,618 B2
(45) Date of Patent: Aug. 9, 2016

(54) TOTAL HIP REPLACEMENT SURGICAL GUIDE TOOL

(75) Inventors: Ilwhan Park, Walnut Creek, CA (US); Michael Koehle, Santa Rosa, CA (US); Lorenzo R. Deveza, San Ramon, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 1953 days.

(21) Appl. No.: 12/391,008

(22) Filed: Feb. 23, 2009

(65) Prior Publication Data

US 2009/0222016 A1    Sep. 3, 2009

Related U.S. Application Data

(60) Provisional application No. 61/032,671, filed on Feb. 29, 2008, provisional application No. 61/108,761, filed on Oct. 27, 2008, provisional application No. 61/111,238, filed on Nov. 4, 2008.

(51) Int. Cl.
| | | |
|---|---|---|
| *A61B 17/17* | (2006.01) | |
| *A61B 17/56* | (2006.01) | |
| *A61B 19/00* | (2006.01) | |
| *A61F 2/36* | (2006.01) | |
| *A61F 2/30* | (2006.01) | |
| *A61F 2/50* | (2006.01) | |

(52) U.S. Cl.
CPC ......... *A61B 17/175* (2013.01); *A61B 2017/568* (2013.01); *A61B 2019/502* (2013.01); *A61B 2019/508* (2013.01); *A61B 2034/102* (2016.02); *A61F 2/3603* (2013.01); *A61F 2002/30878* (2013.01); *A61F 2002/505* (2013.01)

(58) Field of Classification Search
USPC .......................................... 606/87–89; 700/98
See application file for complete search history.

(56) References Cited

U.S. PATENT DOCUMENTS

| | | | |
|---|---|---|---|
| 3,195,411 | A | 7/1965 | MacDonald et al. |
| 3,825,151 | A | 7/1974 | Arnaud |
| D245,920 | S | 9/1977 | Shen |
| 4,198,712 | A | 4/1980 | Swanson |
| 4,298,992 | A | 11/1981 | Burstein |
| 4,436,684 | A | 3/1984 | White |
| D274,093 | S | 5/1984 | Kenna |

(Continued)

FOREIGN PATENT DOCUMENTS

| | | | |
|---|---|---|---|
| DE | 3305237 | A1 | 8/1983 |
| DE | 4341367 | C1 | 6/1995 |

(Continued)

OTHER PUBLICATIONS

U.S. Appl. No. 10/146,862, filed May 15, 2002, Park et al.

(Continued)

*Primary Examiner* — Christian Sevilla
(74) *Attorney, Agent, or Firm* — Polsinelli PC

(57) ABSTRACT

Disclosed herein is a surgical guide tool for use in total hip replacement surgery. The surgical guide tool may include a customized mating region and a resection guide. The customized mating region and the resection guide are referenced to each other such that, when the customized mating region matingly engages a surface area of a proximal femur, the resection guide will be aligned to guide a resectioning of the proximal femur along a preoperatively planned resection plane.

51 Claims, 29 Drawing Sheets

(56) References Cited

U.S. PATENT DOCUMENTS

| | | |
|---|---|---|
| D274,161 S | 6/1984 | Kenna |
| 4,467,801 A | 8/1984 | Whiteside |
| 4,517,969 A | 5/1985 | Halcomb et al. |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A * | 6/1992 | Bert et al. ............ 606/88 |
| 5,123,927 A | 6/1992 | Duncan et al. |
| 5,133,758 A | 7/1992 | Hollister |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| 5,514,140 A | 5/1996 | Lackey |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |

(56) References Cited

U.S. PATENT DOCUMENTS

| | | |
|---|---|---|
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,392,076 B2 | 6/2008 | de La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,548,638 B2 | 6/2009 | Graessner |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,643,862 B2 | 1/2010 | Schoenefeld |
| 7,693,321 B2 | 4/2010 | Lehtonen-Krause |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,787,932 B2 | 8/2010 | Vilsmeier et al. |
| 7,794,467 B2 | 9/2010 | McGinley et al. |
| D626,234 S | 10/2010 | Otto et al. |
| 7,806,896 B1 | 10/2010 | Bonutti |
| 7,842,039 B2 | 11/2010 | Hodorek et al. |
| 7,842,092 B2 | 11/2010 | Otto et al. |
| 7,881,768 B2 | 2/2011 | Lang et al. |
| 7,927,335 B2 | 4/2011 | Deffenbaugh et al. |
| 7,950,924 B2 | 5/2011 | Brajnovic |
| 7,963,968 B2 | 6/2011 | Dees, Jr. |
| D642,263 S | 7/2011 | Park |
| D642,689 S | 8/2011 | Gannoe et al. |
| 8,007,448 B2 | 8/2011 | Moctezuma de La Barrera |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,077,950 B2 | 12/2011 | Tsougarakis et al. |
| 8,086,336 B2 | 12/2011 | Christensen |
| D655,008 S | 2/2012 | Gannoe et al. |
| 8,115,485 B1 | 2/2012 | Maier et al. |
| 8,126,234 B1 | 2/2012 | Edwards et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,152,855 B2 | 4/2012 | Tulkis et al. |
| 8,165,657 B2 | 4/2012 | Krueger |
| 8,170,641 B2 | 5/2012 | Belcher |
| 8,170,716 B2 | 5/2012 | Coste-Maniere et al. |
| 8,177,850 B2 | 5/2012 | Rudan et al. |
| 8,202,324 B2 | 6/2012 | Meulink et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,949 B2 | 9/2012 | Haddad |
| 8,306,601 B2 | 11/2012 | Lang et al. |
| 8,311,306 B2 | 11/2012 | Pavlovskaia et al. |
| 8,323,288 B2 | 12/2012 | Zajac |
| 8,331,634 B2 | 12/2012 | Barth et al. |
| 8,337,501 B2 | 12/2012 | Fitz et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| D691,719 S | 10/2013 | Park |
| 8,545,509 B2 | 10/2013 | Park et al. |
| 8,617,171 B2 | 12/2013 | Park et al. |
| 8,617,175 B2 | 12/2013 | Park et al. |
| 8,702,712 B2 | 4/2014 | Jordan et al. |
| 8,734,455 B2 | 5/2014 | Park et al. |
| 8,737,700 B2 | 5/2014 | Park et al. |
| 8,777,875 B2 | 7/2014 | Park |
| 8,777,955 B2 | 7/2014 | Park |
| 8,801,719 B2 | 8/2014 | Park et al. |
| 8,801,720 B2 | 8/2014 | Park et al. |
| 8,828,011 B2 | 9/2014 | Park et al. |
| 8,882,779 B2 | 11/2014 | Park et al. |
| 8,961,527 B2 | 2/2015 | Park |
| 8,968,320 B2 | 3/2015 | Park et al. |
| 9,014,438 B2 | 4/2015 | Habets |
| 9,017,336 B2 | 4/2015 | Park et al. |
| 9,265,509 B2 | 2/2016 | Park et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0176783 A1 | 9/2003 | Hu |
| 2004/0097952 A1 | 5/2004 | Sarin et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0146369 A1 | 7/2004 | Kato |
| 2004/0147927 A1 | 7/2004 | Tsougarakis et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0153087 A1 | 8/2004 | Sanford et al. |
| 2004/0204760 A1 | 10/2004 | Fitz et al. |
| 2004/0220583 A1 | 11/2004 | Pieczynski, II et al. |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0254584 A1 | 12/2004 | Sarin et al. |
| 2005/0054914 A1 | 3/2005 | Duerk et al. |
| 2005/0059978 A1* | 3/2005 | Sherry et al. .................. 606/87 |
| 2005/0065617 A1 | 3/2005 | de la Barrera et al. |
| 2005/0080426 A1 | 4/2005 | Qian |
| 2005/0113841 A1 | 5/2005 | Sheldon et al. |
| 2005/0148843 A1 | 7/2005 | Roose |
| 2005/0148860 A1 | 7/2005 | Liew et al. |
| 2005/0149091 A1 | 7/2005 | Tanamal et al. |
| 2005/0192588 A1 | 9/2005 | Garcia |

(56) References Cited

U.S. PATENT DOCUMENTS

| | | |
|---|---|---|
| 2005/0201509 A1 | 9/2005 | Mostafavi et al. |
| 2005/0216024 A1 | 9/2005 | Massoud |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015109 A1 | 1/2006 | Haines |
| 2006/0015188 A1 | 1/2006 | Grimes |
| 2006/0030853 A1 | 2/2006 | Haines |
| 2006/0036257 A1 | 2/2006 | Steffensmeier |
| 2006/0079755 A1 | 4/2006 | Stazzone et al. |
| 2006/0110017 A1 | 5/2006 | Tsai et al. |
| 2006/0111628 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0161167 A1 | 7/2006 | Myers |
| 2006/0195113 A1 | 8/2006 | Masini |
| 2006/0244448 A1 | 11/2006 | Ballon et al. |
| 2006/0271058 A1 | 11/2006 | Ashton et al. |
| 2006/0293681 A1 | 12/2006 | Claypool et al. |
| 2007/0005073 A1 | 1/2007 | Claypool et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0106389 A1 | 5/2007 | Croxton et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173853 A1 | 7/2007 | MacMillan |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0211928 A1 | 9/2007 | Weng et al. |
| 2007/0213738 A1 | 9/2007 | Martin et al. |
| 2007/0219560 A1 | 9/2007 | Hodorek |
| 2007/0226986 A1 | 10/2007 | Chi et al. |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0237372 A1 | 10/2007 | Chen et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0137926 A1 | 6/2008 | Skinner et al. |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0208081 A1 | 8/2008 | Murphy |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0085567 A1 | 4/2009 | Kimmlingen et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0125114 A1 | 5/2009 | May et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0209884 A1 | 8/2009 | Van Vorhis et al. |
| 2009/0222014 A1 | 9/2009 | Bojarski et al. |
| 2009/0222015 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0234217 A1 | 9/2009 | Mire et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0285465 A1 | 11/2009 | Haimerl et al. |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0016986 A1 | 1/2010 | Trabish |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0099977 A1 | 4/2010 | Hershberger |
| 2010/0145344 A1 | 6/2010 | Jordan et al. |
| 2010/0152741 A1 | 6/2010 | Park et al. |
| 2010/0153076 A1 | 6/2010 | Bellettre et al. |
| 2010/0153081 A1 | 6/2010 | Bellettre et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0185202 A1 | 7/2010 | Lester et al. |
| 2010/0191242 A1 | 7/2010 | Massoud |
| 2010/0191244 A1 | 7/2010 | White et al. |
| 2010/0198351 A1 | 8/2010 | Meulink |
| 2010/0209868 A1 | 8/2010 | De Clerck |

(56) References Cited

U.S. PATENT DOCUMENTS

| | | |
|---|---|---|
| 2010/0212138 A1 | 8/2010 | Carroll et al. |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0256479 A1 | 10/2010 | Park et al. |
| 2010/0262150 A1 | 10/2010 | Lian |
| 2010/0274253 A1 | 10/2010 | Ure |
| 2010/0274534 A1 | 10/2010 | Steines et al. |
| 2010/0292963 A1 | 11/2010 | Schroeder |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2010/0332194 A1 | 12/2010 | McGuan et al. |
| 2011/0016690 A1 | 1/2011 | Narainasamy et al. |
| 2011/0029091 A1 | 2/2011 | Bojarski et al. |
| 2011/0029093 A1 | 2/2011 | Bojarski et al. |
| 2011/0046735 A1 | 2/2011 | Metzger et al. |
| 2011/0054486 A1 | 3/2011 | Linder-Ganz et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0093108 A1 | 4/2011 | Ashby et al. |
| 2011/0106093 A1 | 5/2011 | Romano et al. |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190775 A1 | 8/2011 | Ure |
| 2011/0190899 A1 | 8/2011 | Pierce et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0305379 A1 | 12/2011 | Mahfouz |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0130434 A1 | 5/2012 | Stemniski |
| 2012/0143197 A1 | 6/2012 | Lang et al. |
| 2012/0143198 A1 | 6/2012 | Boyer et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165820 A1 | 6/2012 | De Smedt et al. |
| 2012/0165821 A1 | 6/2012 | Carignan et al. |
| 2012/0172882 A1 | 7/2012 | Sato |
| 2012/0179147 A1 | 7/2012 | Geebelen et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0221008 A1 | 8/2012 | Carroll et al. |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0197687 A1 | 8/2013 | Pavlovskaia et al. |
| 2013/0345845 A1 | 12/2013 | Park et al. |
| 2014/0005997 A1 | 1/2014 | Park |
| 2014/0078139 A1 | 3/2014 | Park et al. |
| 2014/0081277 A1 | 3/2014 | Park et al. |
| 2014/0128875 A1 | 5/2014 | Park et al. |
| 2014/0324205 A1 | 10/2014 | Park et al. |
| 2014/0330278 A1 | 11/2014 | Park et al. |
| 2014/0330279 A1 | 11/2014 | Park et al. |
| 2014/0378978 A1 | 12/2014 | Park |
| 2016/0015466 A1 | 1/2016 | Park et al. |

FOREIGN PATENT DOCUMENTS

| | | |
|---|---|---|
| DE | 102005023028 A1 | 11/2006 |
| EP | 0097001 A | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| EP | 1669033 A1 | 6/2006 |
| FR | 2478462 A1 | 9/1981 |
| GB | 2215610 A1 | 9/1989 |
| GB | 2420717 A | 6/2006 |
| GB | 2447702 A | 9/2008 |
| JP | 10-94538 | 4/1998 |
| JP | 2001-092950 | 4/2001 |
| JP | P2005-287813 | 10/2005 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 98/32384 | 7/1998 |
| WO | WO 00/35346 | 6/2000 |
| WO | WO 01/00096 A1 | 1/2001 |

(56) References Cited

FOREIGN PATENT DOCUMENTS

| | | |
|---|---|---|
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2005/099636 A1 | 10/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/127486 A2 | 11/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2007/097854 A2 | 8/2007 |
| WO | WO 2007/137327 A1 | 12/2007 |
| WO | WO 2008/014618 A1 | 2/2008 |
| WO | WO 2008/091358 A1 | 7/2008 |

OTHER PUBLICATIONS

U.S. Appl. No. 29/296,687, filed Oct. 25, 2007, Park.
U.S. Appl. No. 12/111,924, filed Apr. 29, 2008, Park et al.
U.S. Appl. No. 12/390,667, filed Feb. 23, 2009, Park et al.
U.S. Appl. No. 12/386,105, filed Apr. 14, 2009, Pavlovskaia et al.
U.S. Appl. No. 12/505,056, filed Jul. 17, 2009, Park.
International Search Report and Written Opinion, International Application No. PCT/US2009/040629, mailed Aug. 6, 2009, 9 pages.
Restriction Requirement, U.S. Appl. No. 11/641,382, mailed Sep. 3, 2009, 6 pages.
Restriction Requirement, U.S. Appl. No. 11/642,385, mailed Oct. 27, 2009, 7 pages.
International Search Report and Written Opinion, International Application No. PCT/US2009/051109, mailed Nov. 6, 2009, 13 pages.
NonFinal Office Action, U.S. Appl. No. 11/641,569, mailed Nov. 12, 2009, 9 pages.
Restriction Requirement, U.S. Appl. No. 11/656,323, mailed Nov. 13, 2009, 10 pages.
Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Final Office Action and PTO-892, U.S. Appl. No. 11/641,382, mailed Aug. 5, 2010, 13 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2011/032342, dated Jul. 1, 2011, 8 pages.
Non-Final Office Action and PTO-892, U.S. Appl. No. 11/641,382, mailed Jan. 20, 2010, 12 pages.
NonFinal Office Action and PTO-892, U.S. Appl. No. 11/642,385, mailed Mar. 2, 2010, 11 pages.
Non-Final Office Action and PTO-892, U.S. Appl. No. 11/656,323, mailed Mar. 30, 2010, 10 pages.
Nonfinal Office Action, U.S. Appl. No. 11/959,344, dated Feb. 15, 2011, 29 pages.
Notice of Allowance, U.S. Appl. No. 29,296,687, mailed Mar. 31, 2011, 18 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Application No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/641,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Restriction Requirement, U.S. Appl. No. 11/959,344, dated Oct. 29, 2010, 6 pages.
Restriction Requirement, U.S. Appl. No. 29/296,687, mailed Sep. 21, 2010, 7 pages.
Restriction Requirement, U.S. Appl. No. 12/390,667, dated Jul. 14, 2011, 9 pages.
AKCA, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.

(56) References Cited

OTHER PUBLICATIONS

Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage vol. as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res. 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical orthop Relat Res. 2003(410):35-43.
Freeman et al., "The movement of the Normal Tibio-Femoral Joint," Journal Biomech. 2005;38(2):197-208.
Graichen et al., "quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "least Squares 3D Surface and Curve Matching," ISPRS Journal of Photogrammetry & Remote Sensing, 59(2005), 151-174.
Hollister et al., "The Axes of Rotation of the Knee," Clin Orthop Relat Res. 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using a 2d/3d Database", Dept. of Surgery, Trauma Unit, University Hospital, Bassel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
U.S. Appl. No. 12/546,545, filed Aug. 24, 2009, Park et al.

(56) References Cited

OTHER PUBLICATIONS

U.S. Appl. No. 12/563,809, filed Sep. 21, 2009, Park et al.
Office Action, U.S. Appl. No. 10/146,862, mailed Jan. 13, 2005, 10 pages.
Amendment and Response to Office Action and Petition to Revive, U.S. Appl. No. 10/146,862, filed Jan. 18, 2006, 29 pages.
Restriction Requirement, U.S. Appl. No. 11/641,569, mailed Apr. 27, 2009, 7 pages.
International Search Report and Written Opinion, PCT/US2008/083125, dated Mar. 9, 2009, 13 pages.
International Search Report and Written Opinion, International Application No. PCT/US2009/34983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
Akenine-Möller et al., Real-Time Rendering, Second Edition, AK Peters, Natick, MA, 6 pages (Table of Contents), 2002.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," Computer Aided Geometric Design, vol. 12, pp. 207-229, 1995.
Barequet et al., "Repairing CAD Models," Proceedings of the 8th IEEE Visualization '97 Conference, pp. 363-370, Oct. 1997.
Berry et al., "Personalised image-based templates for intra-operative guidance," Proc. Inst. Mech. Eng. Part H: J. Engineering in Medicine, vol. 219, pp. 111-118, Oct. 7, 2004.
Biščević et al., "Variations of Femoral Condyle Shape," Coll. Antropol., vol. 29 No. 2, pp. 409-414, 2005.
Blinn, Jim Blinn's Corner—A Trip Down the Graphics Pipeline, Morgan Kaufmann Publishers, Inc., San Francisco, CA, 5 pages (Table of Contents), 1996.
Bøhn et al., "A Topology-Based Approach for Shell-Closure," Geometric Modeling for Product Realization (P.R. Wilson et al. editors), pp. 297-319, Elsevier Science Publishers B.V., North-Holland, 1993.
Chauhan et al., "Computer-assisted knee arthroplasty versus a conventional jig-based technique—a randomised, prospective trial," The Journal of Bone and Joint Surgery, vol. 86-B, No. 3, pp. 372-377, Apr. 2004.
Cohen et al., Radiosity and Realistic Image Synthesis, Academic Press Professional, Cambridge, MA, 8 pages (Table of Contents), 1993.
Couglin et al., "Tibial Axis and Patellar Position Relative to the Femoral Epicondylar Axis During Squatting," The Journal of Arthroplasty, vol. 18, No. 8, Elsevier, 2003.
Delp et al., "Computer Assisted Knee Replacement," Clinical Orthopaedics and Related Research, No. 354, pp. 49-56, Sep. 1998.
Dutré et al., Advanced Global Illumination, AK Peters, Natick, MA, 5 pages (Table of Contents), 2003.
Eckhoff et al., "Three-Dimensional Mechanics, Kinematics, and Morphology of the Knee Viewed in Virtual Realty," The Journal of Bone and Joint Surgery, vol. 87-A, Supplement 2, pp. 71-80, 2005.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., Landscape Modeling, McGraw-Hill, New York, NY, 8 pages (Table of Contents), 2001.
Farin, Nurb Curves and Surfaces: From Projective Geometry to Practical Use, AK Peters, Wellesley, MA, 7 pages (Table of Contents), 1995.
Fleischer et al., "Accurate Polygon Scan Conversion Using Half-Open Intervals," Graphics Gems III, pp. 362-365, code: pp. 599-605, 1992.
Foley et al., Computer Graphics: Principles and Practice, Addison-Wesley Publishing Company, Reading, MA, 9 pages (Table of Contents), 1990.
Glassner (editor), An Introduction to Ray Tracing, Academic Press Limited, San Diego, CA, 4 pages (Table of Contents), 1989.
Glassner, Principles of Digital Image Synthesis, vols. One and Two, Morgan Kaufmann Publishers, Inc., San Francisco, CA, 32 pages (Table of Contents), 1995.
Gooch et al., Non-Photorealistic Rendering, AK Peters, Natick, MA, 4 pages (Table of Contents), 2001.
Grüne et al., "On numerical algorithm and interactive visualization for optimal control problems," Journal of Computation and Visualization in Science, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: Fact and Fiction Syllabus, San Diego, CA, 8 pages, Oct. 20-22, 2005 (best available copy).
Hafez et al., "Computer Assisted Total Knee Replacement: Could a Two-Piece Custom Template Replace the Complex Conventional Instrumentations?", Computer Aided Surgery, vol. 9, No. 3, pp. 93-94, 2004.
Hafez et al., "Computer-Assisted Total Knee Arthroplasty Using Patient-Specific Templating," Clinical Orthopaedics and Related Research, No. 0, pp. 1-9, 2006.
Jensen, Realistic Image Synthesis Using Photon Mapping, AK Peters, Natick, MA, 7 pages (Table of Contents), 2001.
Jones et al., "A new approach to the construction of surfaces from contour data," Computer Graphics Forum, vol. 13, No. 3, pp. 75-84, 1994 [ISSN 0167-7055].
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," Advanced Sensor and Control-System Interface (B.O. Nnaji editor), Proceedings SPIE—The International Society for Optical Engineering, Bellingham, WA, vol. 2911, pp. 9-22, Nov. 21-22, 1996.
Kumar, Robust Incremental Polygon Triangulation for Surface Rendering, Center for Geometric Computing, Department of Computer Science, Johns Hopkins University, Baltimore, MD, WSCG, The International Conference in Central Europe on Computer Graphics, Visualization and Computer Vision, pp. 381-388, 2000.
Kunz et al., "Computer Assisted Hip Resurfacing Using Individualized Drill Templates," The Journal of Arthroplasty, vol. 00, No. 0, pp. 1-7, 2009.
Lorensen et al., "Marching Cubes: A High Resolution 3d Surface Construction Algorithm," Computer Graphics, vol. 21, No. 4, pp. 163-169, 1987.
Nooruddin et al., Simplification and Repair of Polygonal Models Using Volumetric Techniques, IEEE Transactions on Visualization and Computer Graphics, vol. 9, No. 2, pp. 191-205, Apr.-Jun. 2003.
Pharr et al., Physically Based Rendering, from Theory to Implementation, Morgan Kaufmann Publishers, San Francisco, CA, 13 pages (Table of Contents), 2004.
Platt et al., "Mould Arthroplasty of the Knee, A Ten-Year Follow-up Study," The Journal of Bone and Joint Surgery (British Volume), vol. 51-B, No. 1, pp. 76-87, Feb. 1969.

(56) References Cited

OTHER PUBLICATIONS

Potter, "Arthroplasty of the Knee with Tibial Metallic Implants of the McKeever and Macintosh Design," The Surgical Clinics of North America, vol. 49, No. 4, pp. 903-915, Aug. 1969.
Radermacher et al., "Computer Assisted Orthopaedic Surgery with Image Based Individual Templates," Clinical Orthopaedics and Related Research, vol. 354, pp. 28-38, Sep. 1998.
Rohlfing et al., "Quo Vadis, Atlas-Based Segmentation?", The Handbook of Medical Image Analysis: Segmentation and Registration Models (Kluwer), pp. 1-55, (http://www.stanford.edu/~rohlfing/publications/2005-rohlfing-chapter-quo_vadis_atlas_based_segmentation.pdf).
Shirley et al., Realistic Ray Tracing, Second Edition, AK Peters, Natick, MA, 7 pages (Table of Contents), 2003.
Strothotte et al., Non-Photorealistic Computer Graphics—Modeling, Rendering, and Animation, Morgan Kaufmann Publishers, San Francisco, CA, 9 pages (Table of Contents), 2002.
Vande Berg et al., "Assessment of Knee Cartilage in Cadavers with Dual-Detector Spiral CT Arthrography and MR Imaging," Radiology, vol. 222, No. 2, pp. 430-436, Feb. 2002.
Wikipedia, the Free Encyclopedia, "CNC," (date unknown) located at http://en.wikipedia.org/wiki/CNC>, 6 pages, last visited on Apr. 12, 2007.
Non-Final Office Action, U.S. Appl. No. 11/641,569, dated Aug. 3, 2011, 14 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 11/946,002, dated Nov. 25, 2011, 44 pages.
Non-Final Office Action, U.S. Appl. No. 12/386,105, dated Feb. 9, 2012, 30 pages.
Notice of Allowance, U.S. Appl. No. 13/066,568, mailed Oct. 26, 2011, 28 pages.
Office Action (Restriction Requirement), U.S. Appl. No. 12/563,809, dated Feb. 2, 2012, 7 pages.
Response to Final Office Action, U.S. Appl. No. 11/959,344, filed Dec. 27, 2011, 16 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Restriction Requirement, U.S. Appl. No. 12/386,105, filed Dec. 21, 2011, 9 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/386,105, dated Oct. 24, 2011, 7 pages.
Amendment Under 37 C.F.R. 1.312, U.S. Appl. No. 12/386,105, filed Oct. 1, 2012, 6 pages.
Non-Final Office Action, U.S. Appl. No. 12/390,667, mailed Sep. 26, 2012, 21 pages.
Non-Final Office Action, U.S. Appl. No. 12/563,809, mailed Sep. 21, 2012, 32 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 13/374,960, mailed Nov. 2, 2012, 24 pages.
RCE/Amendment, U.S. Appl. No. 11/946,002, filed Sep. 6, 2012, 38 pages.
Response to Final Office Action, U.S. Appl. No. 11/641,382, filed Sep. 24, 2012, 11 pages.
Response to Final Office Action, U.S. Appl. No. 11/924,425, filed Sep. 5, 2012, 9 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
U.S. Appl. No. 13/488,505, filed Jun. 5, 2012, Ilwhan Park et al.
Appeal Brief, U.S. Appl. No. 12/390,667, filed Jul. 12, 2012, 32 pages.
Final Office Action, U.S. Appl. No. 11/641,382, mailed Jul. 25, 2012, 12 pages.
Final Office Action, U.S. Appl. No. 11/924,425, mailed Jul. 6, 2012, 14 pages.
Non-Final Office Action, U.S. Appl. No. 12/111,924, mailed Jun. 29, 2012, 35 pages.
Non-Final Office Action, U.S. Appl. No. 12/546,545, mailed Jul. 19, 2012, 28 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 12/386,105, mailed Jul. 5, 2012, 11 pages.
Response to Final Office Action, U.S. Appl. No. 11/641,569, filed Jun. 28, 2012, 10 pages.
Response to Non-Final Office Action, U.S. Appl. No. 12/386,105, filed Jun. 8, 2012, 13 pages.
Response to Non-Final Office Action, U.S. Patent Application No. 11/641,382, filed Jun. 27, 2012, 12 pages.
Response to Restriction, U.S. Appl. No. 12/563,809, filed Aug. 6, 2012, 10 pages.
Response to Restriction, U.S. Appl. No. 12/546,545, filed Jun. 4, 2012, 7 pages.
Restriction Requirement, U.S. Appl. No. 12/563,809, mailed Jul. 6, 2012, 6 pages.
U.S. Appl. No. 13/573,662, filed Oct. 2, 2012, Pavlovskaia et al.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Non-Final Office Action, U.S. Appl. No. 11/641,569, dated Jan. 3, 2013, 12 pages.
Non-Final Office Action, U.S. Appl. No. 13/086,275, mailed Feb. 7, 2013, 36 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.
Response to Non-Final Office Action, U.S. Appl. No. 12/563,809, filed Dec. 13, 2012, 15 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.

(56) References Cited

OTHER PUBLICATIONS

Audette et al. "An algorithmic overview of surface registration techniques for medical imaging." Medical Image Analysis, vol. 4, No. 3, Sep. 1, 2000, pp. 201-217.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Calvo et al., "High Resolution MRI Detects Cartilage Swelling at the Early Stages of Experimental Osteoarthritis," OARSI, 2001, pp. 463-472.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al.. "Prediction of Total Knee Motion Using a Three-Dimensional Computer-Graphics Model." *J. Biomechanics*, vol. 23, No. 1, pp. 45-58, 1990.
Ibanez et al., The ITK Software Guide, Second Edition, Updated for ITK version 2.4, Nov. 21, 2005, pp. 114, 396-411, and 426.
Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Siemens MAGNETOM Sonata 1.5T Technical Specifications, pp. 1-4, accessed online Jan. 28, 2014.
Walker, P. S. et al. "Range of Motion in Total Knee Arthroplasty: A Computer Analysis." *Clinical Orthopaedics and Related Research*, No. 262, Jan. 1991.
Xie et al. "Segmentation by surface-to-image registration." proceedings of SPIE, vol. 6144, Mar. 2, 2006, pp. 614405-1-614405-7.
Advisory Action and Interview Summary, U.S. Appl. No. 12/390,667, mailed Apr. 27, 2012, 23 pages.
Advisory Action, U.S. Appl. No. 11/642,385, dated Aug. 1, 2014.
Amendment and Response After Final Office Action, U.S. Appl. No. 11/656,323, dated Aug. 25, 2014.
Amendment Under 37 C.F.R. 1.312, U.S. Appl. No. 13/374,960, filed May 7, 2013, 6 pages.
Amendment Under 37 CFR 1.312, U.S. Appl. No. 14/824,731, dated Dec. 28, 2015.
Appeal Brief, U.S. Appl. No. 11/642,385, dated Oct. 7, 2014.
Australian Patent Examination Report No. 1, AU 2013200861, dated Mar. 3, 2015.
Canadian Office Action, Appl. No. 2642616, dated Apr. 22, 2015.
Canadian Office Action, Appl. No. 2708393, dated Jul. 29, 2014.
Canadian Office Action, CA2708393, dated May 7, 2015.
Canadian Office Action, CA2721735, dated Jul. 7, 2015.
Canadian Office Action, CA2721762, dated Nov. 10, 2015.
EP Communication pursuant to Article 94(3) EPC, EP10192631.9, dated Feb. 12, 2016.
European Examination Report, EP10192631.9, dated Feb. 11, 2015.
European Patent Office, Summons to Attend Oral Proceedings, EP07749030.8, dated Sep. 10, 2015.
European Search Report, EP 09835583.7, dated May 9, 2014.
European Search Report, EP09718014.5, dated May 13, 2015.
European Search Report, EP09718041.8, dated May 12, 2015.
European Search Report, EP09739422.5, dated Mar. 28, 2013, 9 pages.
European Search Report, EP09823986.6, dated Sep. 23, 2014.
European search Report, European Appl. No. 08863202.1, dated May 16, 2014.
Extended European Search Report, European Appl. No. 13188389.4, dated Jan. 8, 2014.
Final Office Action, U.S. Appl. No. 11/641,569, dated Nov. 29, 2013, 20 pages.
Final Office Action, U.S. Appl. No. 11/641,569, mailed Mar. 1, 2012, 12 pages.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 11/946,002, dated Sep. 17, 2014.
Final Office Action, U.S. Appl. No. 11/946,002, mailed May 9, 2012, 24 pages.
Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 12/563,809, mailed Mar. 7, 2013, 14 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Final Office Action, U.S. Appl. No. 11/946,002, dated Nov. 30, 2015.
Final Rejection, U.S. Appl. No. 13/749,095, dated Dec. 24, 2015.
Final Rejection, U.S. Appl. No. 14/476,500, dated Feb. 1, 2016.
International Search Report and Written Opinion, PCT/US2014/030496, dated Aug. 6, 2014.
Japanese Office Action, JP Application No. 2011-507530, dated Dec. 17, 2013, 8 pages.
Japanese Office Action, JP2014-147908, dated Jun. 9, 2015.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 11/641,382, mailed Mar. 29, 2012, 24 pages.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/656,323, dated Sep. 18, 2014.
Non-Final Office Action, U.S. Appl. No. 11/946,002, dated Oct. 2, 2013, 39 pages.
Non-Final Office Action, U.S. Appl. No. 11/946,002, dated Feb. 6, 2014, 46 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/546,545, mailed Mar. 13, 2013, 10 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/488,505, dated Jul. 17, 2014.
Non-Final Office Action, U.S. Appl. No. 13/723,904, mailed Aug. 9, 2013, 6 pages.
Non-Final Office Action, U.S. Appl. No. 13/730,467, dated Jan. 15, 2014, 8 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Non-Final Office Action, U.S. Appl. No. 11/946,002, dated Jun. 29, 2015.
Non-Final Office Action, U.S. Appl. No. 13/749,095, dated Sep. 10, 2015.
Non-Final Office Action, U.S. Appl. No. 13/923,093, dated Dec. 2, 2015.
Non-Final Office Action, U.S. Appl. No. 13/960,498, dated Feb. 9, 2016.
Non-Final Office Action, U.S. Appl. No. 14/011,998, dated Feb. 12, 2016.
Non-Final Office Action, U.S. Appl. No. 14/084,255, dated Feb. 25, 2016.
Non-Final Office Action, U.S. Appl. No. 14/476,500, dated Jun. 18, 2015.
Notice of Allowance, U.S. Appl. No. 11/656,323, dated Feb. 3, 2015.

(56) References Cited

OTHER PUBLICATIONS

Notice of Allowance, U.S. Design Appl. No. 29/394,882, mailed May 24, 2013, 16 pages.
Notice of Allowance, U.S. Appl. No. 11/641,569, dated Feb. 5, 2014, 11 pages.
Notice of Allowance, U.S. Appl. No. 11/959,344, mailed Mar. 5, 2012, 13 pages.
Notice of Allowance, U.S. Appl. No. 12/111,924, mailed Mar. 11, 2013, 14 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/563,809, mailed May 28, 2013, 11 pages.
Notice of Allowance, U.S. Appl. No. 12/636,939, dated Oct. 7, 2013, 28 pages.
Notice of Allowance, U.S. Appl. No. 12/760,388, dated Jan. 22, 2014, 13 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Notice of Allowance, U.S. Appl. No. 13/731,697, dated Jul. 29, 2015.
Notice of Allowance, U.S. Appl. No. 14/824,731, dated Oct. 20, 2015.
Preliminary Amendment, U.S. Appl. No. 13/731,697, filed May 10, 2013, 6 pages.
Preliminary Amendment, U.S. Appl. No. 13/731,850, filed Apr. 11, 2014, 8 pages.
Reply Brief, U.S. Appl. No. 11/642,385, dated Jan. 23, 2015.
Response to Final Office Action, U.S. Appl. No. 12/546,545, filed Feb. 20, 2013, 13 pages.
Response to Final Office Action, U.S. Appl. No. 11/641,569, dated Jan. 29, 2014, 10 pages.
Response to Final Office Action, U.S. Appl. No. 11/642,385, dated Jul. 22, 2014.
Response to Final Office Action, U.S. Appl. No. 12/390,667, dated Dec. 23, 2013, 5 page.
Response to Final Office Action, U.S. Appl. No. 12/390,667, filed Mar. 12, 2012, 19 pages.
Response to Final Office Action, U.S. Appl. No. 12/563,809, filed May 6, 2013, 15 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 12/636,939, filed Apr. 8, 2013, 10 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Final Office Action, U.S. Appl. No. 13/749,095, dated Feb. 17, 2016.
Response to Non-Final Office Action, U.S. Appl. No. 13/731,697, dated May 26, 2015.
Response to Non-Final Office Action, U.S. Appl. No. 13/749,095, dated Apr. 20, 2015.
Response to Non-Final Office Action, U.S. Appl. No. 12/390,667, filed Feb. 26, 2013, 36 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 11/946,002, dated Sep. 29, 2015.
Response to Non-Final Office Action, U.S. Appl. No. 14/476,500, dated Oct. 16, 2015.
Response to Restriction Requirement, U.S. Appl. No. 12/760,388, filed Apr. 5, 2013, 7 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 14/476,500, dated Mar. 17, 2015.
Response to Restriction, U.S. Appl. No. 13/749,095, dated Nov. 13, 2014.
Response to Restriction, U.S. Appl. No. 12/505,056, filed Apr. 11, 2012, 9 pages.
Response to Restriction, U.S. Appl. No. 13/488,505, dated May 5, 2014, 7 pages.
Response to Restriction, U.S. Appl. No. 13/960,498, dated Nov. 19, 2015.
Restriction Requirement, U.S. Appl. No. 14/476,500, dated Feb. 25, 2015.
Restriction Requirement, U.S. Appl. No. 12/111,924, mailed Mar. 19, 2012, 8 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/636,939, mailed Apr. 13, 2012, 6 pages.

(56) References Cited

OTHER PUBLICATIONS

Restriction Requirement, U.S. Appl. No. 12/760,388, mailed Mar. 6, 2013, 7 pages.
Restriction Requirement, U.S. Appl. No. 13/488,505, dated Mar. 4, 2014, 5 pages.
Restriction Requirement, U.S. Appl. No. 13/749,095, dated Sep. 25, 2014.
Restriction Requirement, U.S. Appl. No. 13/960,498, dated Sep. 23, 2015.
Supplementary European Search Report and Opinion, EP 09739474.6, dated Feb. 27, 2014, 7 pages.
Taylor et al., "Computer-integrated revision total hip replacement surgery: concept and preliminary results," Medical Image Analysis (1999) vol. 3, No. 3, pp. 301-319.
Non-Final Office Action, U.S. Appl. No. 11/946,002, dated May 18, 2016.
Non-Final Office Action, U.S. Appl. No. 14/869,762, dated Mar. 31, 2016.
Notice of Allowance, U.S. Appl. No. 13/749,095, dated Apr. 7, 2016.
Notice of Allowance, U.S. Appl. No. 14/476,500, dated May 19, 2016.
Response to Non-Final Office Action, U.S. Appl. No. 13/923,093, dated May 2, 2016.
Response to Non-Final Office Action, U.S. Appl. No. 14/011,998, dated May 6, 2016.
Response to Non-Final Office Action, U.S. Appl. No. 14/084,255, dated May 23, 2016.

* cited by examiner

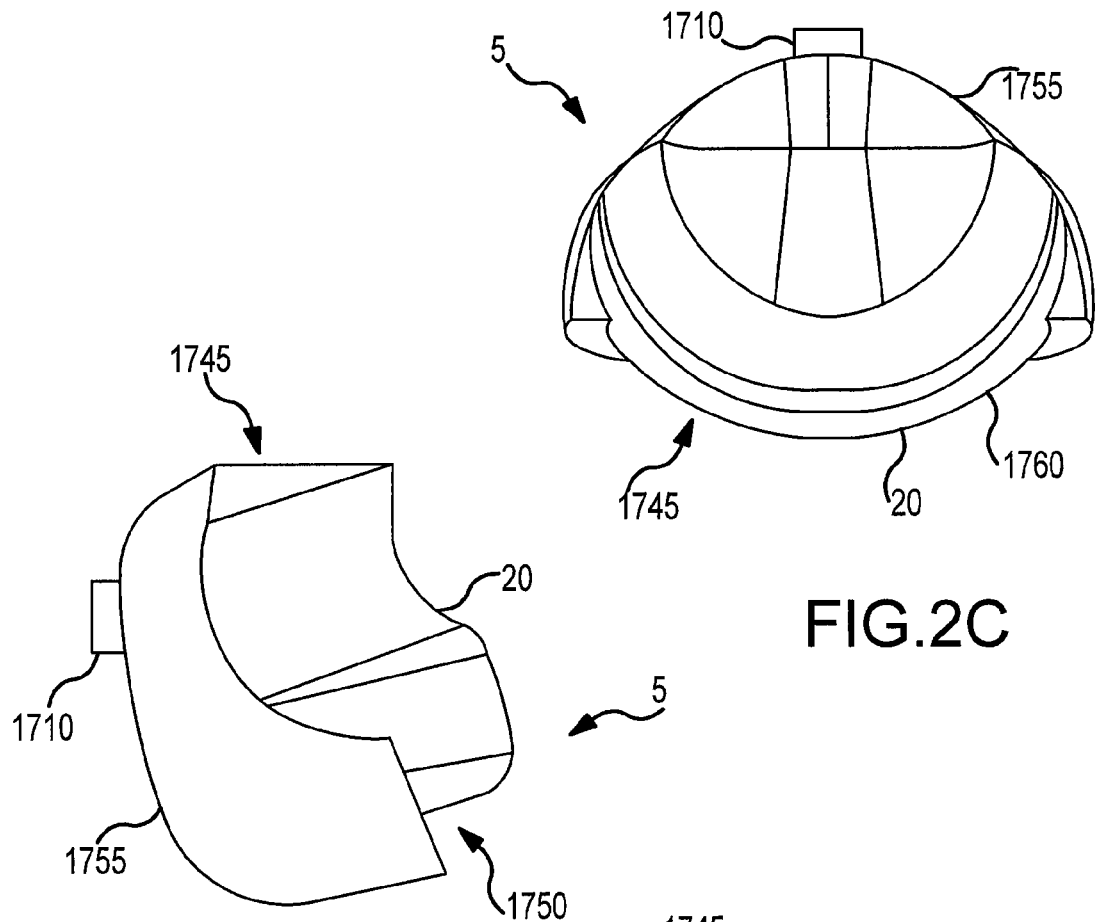
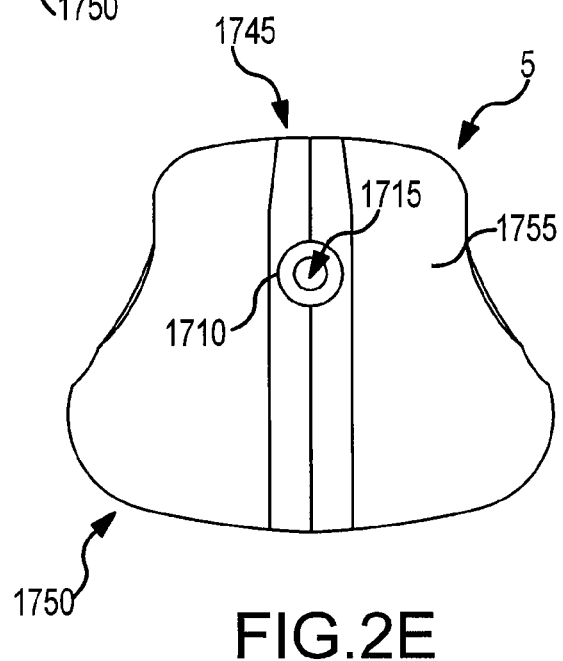
FIG.2C
FIG.2D
FIG.2E

TOTAL HIP REPLACEMENT SURGICAL GUIDE TOOL

CROSS REFERENCE TO RELATED APPLICATIONS

The present application claims benefit of priority under 35 U.S.C. 119(e) to: U.S. Patent Application 61/032,671, entitled Hip Resurfacing Surgical Guide Tool and filed Feb. 29, 2008; U.S. Patent Application 61/108,761, entitled Hip Resurfacing Surgical Guide Tool and filed Oct. 27, 2008; and U.S. Patent Application 61/111,238, entitled Total Hip Replacement Surgical Guide Tool and filed Nov. 4, 2008. The foregoing applications are hereby incorporated by reference into the present application in their entireties.

The present application also incorporates by reference in its entirety copending U.S. patent application Ser. No. 12/390,667, entitled Hip Resurfacing Surgical Guide Tool, and filed on the same date as the present application, namely, Feb. 23, 2009.

FIELD OF THE INVENTION

The present invention relates to medical apparatus and methods. More specifically, the present invention relates to total hip replacement surgical guide tools and methods of manufacturing and using such tools.

BACKGROUND OF THE INVENTION

Arthroplasty is an orthopedic surgical procedure in which a dysfunctional or arthritic joint surface is replaced, remodeled or redesigned to alleviate pain, restore range of motion or to fix physical joint damage caused by a fracture. Total Hip Replacement ("THR") surgery, also known as hip arthroplasty, is a surgical procedure wherein the proximal femur, with its femoral head and neck, is removed and a prosthetic device (or stem) having a prosthetic femoral head is implanted into the femur. The acetabulum, or hip socket, is also replaced or modified to accept a cup. The cup is configured to receive the prosthetic head. The prosthetic device (or stem) is typically made of titanium or a titanium alloy. The head may be made of a biocompatible plastic, ceramic or other suitable material. The cup may be made of a biocompatible plastic or other suitable material. The prosthetic device and the cup are typically anchored to the bone with bone cement.

Typically, in THR, the surgeon will take a number of measurements by hand or x-ray scan related to proper selection of the prosthetic device, limb length, and hip rotation. During surgery, after making an incision, the femur is pushed out of socket to expose the joint cavity and the deteriorated or damaged femoral head is removed. The femur is then prepared to receive the stem by cleaning and enlarging the hollow center portion of the bone, thereby creating a cavity that matches the shape of the implant stem. The top end of the femur is planed and smoothed so the stem can be inserted flush with the bone surface. If the head is a separate piece, the proper size is selected and attached. Finally, the head is seated within the cup so the joint is properly aligned and the incision is closed.

Hand measuring techniques and x-ray scans are inaccurate and increase the error rate or potential for error in a THR, and may lead to an improperly positioned prosthetic device. Improper positioning of the prosthetic device can result in a change of leg length, dislocation of the hip or perforation of the femur.

There is a need in the art for a total hip replacement surgical guide tool to aid in properly positioning the prosthetic device that reduces the potential for error and improper positioning in a THR. There is also a need in the art for a method of manufacturing such a surgical guide tool.

BRIEF SUMMARY OF THE INVENTION

Disclosed herein is a tool for positioning a prosthetic device in a femur that is the subject of a total hip replacement surgery. In one embodiment, the tool includes an index surface and a saw slot. The index surface is configured to matingly receive a predetermined surface of the femur. The index surface and the saw slot are integrated with each other such that when the index surface matingly receives the predetermined surface of the femur, the saw slot corresponds with the resection plane of the femur.

Disclosed herein is surgical guide tool for use in the preparation of a proximal portion of a femur for the implantation of a total hip replacement prosthetic implant, the implant including a feature configured to abut against a resection surface of the proximal femur when the implant is fully implanted in the proximal femur in a manner that generally replicates a preoperatively planned implantation for the implant. In one embodiment, the tool includes a mating region and a saw guide. When the mating region matingly contacts the proximal portion, the saw guide is aligned with a resection plane generally corresponding to the resection surface. In one version of the embodiment, the saw guide includes at least one planar surface. In one version of the embodiment, the at least one planar surface forms a saw slot.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck. The at least a portion of a superior-posterior region of the neck starts between approximately 1 mm and approximately 5 mm after a cartilage covering the head terminates distally and extending between approximately 15 mm and approximately 35 mm towards a trochanteric fossa. In version of the embodiment, the saw guide includes at least one planar surface. In one version of the embodiment, the at least a portion of a superior-posterior region of the neck has an inferior border that begins approximately midway along an intertrochanteric crest and follows along the axis of the neck. In one version of the embodiment, the at least a portion of a superior-posterior region of the neck has a superior border between approximately 1 mm and approximately 3 mm below a junction between superior and anterior surfaces of the neck.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck. The at least a portion of a superior-posterior region of the neck includes a narrow band that follows along an intertrochanteric crest and has a medial-lateral width of between approximately 0.5 mm and approximately 8 mm. In one version of the embodiment, the saw guide includes at least one planar surface. In one version of the embodiment, the at least a portion of a superior-posterior region of the neck begins approximately midway along the intertrochanteric crest and extends at least approximately 5 mm towards a most superior tip of a posterior surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-anterior region of the neck. The at least a portion of a superior-anterior region of the neck starts between approximately 1 mm and approximately 5 mm after a cartilage covering the head terminates distally and extends between approximately 15 mm and approximately 35 mm to terminate before a tubercle. In one version of the embodiment, the saw guide includes at least one planar surface. In one version of the embodiment, the at least a portion of a superior-anterior region of the neck has a superior border approximately 1 mm to approximately 3 mm below a junction between superior and anterior surfaces of the neck. The at least a portion of a superior-anterior region of the neck may have an inferior border that is between approximately 5 mm and approximately 10 mm from the superior boarder. In one version of the embodiment, the at least a portion of a superior-anterior region of the neck lies on an anterior greater trochanter, distal to a tubercle, and inferior to an origin of an obturator internus. The at least a portion of a superior-anterior region may have a medial-lateral distance that measures between approximately 3 mm to approximately 14 mm. The at least a portion of a superior-anterior region may have an inferior-superior distance that measures between approximately 3 mm to approximately 10 mm.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck and at least a portion of a superior-anterior region of the neck, but does not include a junction between the superior-posterior and superior-anterior regions of the neck. In one version of the embodiment, the saw guide includes at least one planar surface. In one version of the embodiment, the at least a portion of the superior-posterior region of the neck includes an area that extends along the intertrochanteric chest, but does not include an area that spans portions of a trochanteric fossa. The at least a portion of a superior-anterior region of the neck may lay on an anterior greater trochanter, distal to a tubercle, and inferior to an origin of an obturator internus, but does not include portions of the tubercle.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that extends towards a trochanteric fossa between approximately 15 mm and approximately 35 mm from a first point being between approximately 1 mm and approximately 5 mm distal of a distal termination of a cartilage covering the head. In one version of the embodiment, the saw guide includes at least one planar surface. In one version of the embodiment, the at least a portion of a posterior region of the neck has an inferior border that terminates up to approximately 5 mm superior to a border between posterior and inferior surfaces of the neck. In one version of the embodiment, the at least a portion of a posterior region of the neck has a superior border that terminates approximately 0 mm to approximately 5 mm posterior of a border between posterior and anterior surfaces of the neck. In one version of the embodiment, the at least a portion of a posterior region of the neck extends along an intertrochanteric crest from a lesser trochanter to a point near a tip of a greater trochanter. The at least a portion of a posterior region of the neck does not include at least one of a portion of the trochanteric fossa and a portion of posterior region of the greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that includes a narrow band measuring between approximately 0.5 mm and approximately 12 mm and following along an intertrochanteric crest. In one version of the embodiment, the saw guide includes at least one planar surface. In one version of the embodiment, the narrow band begins approximately 0 mm to approximately 12 mm superior to a lesser trochanter. The narrow band may extend approximately 0 mm to approximately 18 mm inferior to a most superior tip of a posterior surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that extends towards a trochanteric fossa from a first point being between approximately 1 mm and approximately 5 mm distal of a distal termination of a cartilage covering the head, but does not include an area spanning portions of the trochanteric fossa. In one version of the embodiment, the saw guide includes at least one planar surface. In one version of the embodiment, The tool of claim 32, wherein the area spanning portions of the trochanteric fossa has a width generally transverse to a femoral longitudinal axis of between approximately 0 mm and approximately 20 mm. In one version of the embodiment, the at least a portion of the posterior region of the neck further includes an area that includes a band following along an intertrochanteric crest, but does not include portions of a posterior greater trochanter. In one version of the embodiment, the portion of the posterior greater trochanter has a distally extending dimension of between approximately 0 mm and approximately 12 mm.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of an anterior region of the neck. The at least a portion of an anterior region of the neck extends up to approximately 8 mm laterally past an intertrochanteric line. In one version of the embodiment, the saw guide includes at least one planar surface. In one version of the embodiment, the surface region includes a medial surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a lateral posterior greater trochanter. In one version of the embodiment, the saw guide includes at least one planar surface. In one version of the embodiment, the surface region further includes at least a portion of a medial posterior greater trochanter. The surface region may not include at least a portion of an intertrochanteric crest. In one version of the embodiment, the surface region further includes at least a portion of a posterior region of the neck. The surface region does not include at least a portion of a trochanteric fossa. In one version of the embodiment, the surface region further includes at least a portion of a medial posterior greater trochanter and at least a portion of a posterior region of the neck, and wherein the surface region does not include at least a portion of an intertrochanteric crest and does not include at least a portion of an trochanteric fossa.

Disclosed herein is a surgical guide tool for use in total hip replacement surgery on a proximal portion of a femur. In one embodiment, the tool includes a mating region and a saw guide. The mating region matingly contacts the proximal portion. The saw guide is generally aligned with a preoperatively planned resection plane. In one version of the embodiment, the saw guide includes at least one planar surface. The at least one planar surface may form a saw slot. In one version of the embodiment, the mating region includes contact surfaces and non-contact surfaces, wherein, when the mating region matingly contacts the proximal portion, the contact surfaces matingly contact surfaces of the proximal portion opposing the contact surfaces, and the non-contact surfaces are spaced apart from surfaces of the proximal portion opposing the non-contact surfaces. The non-contact surfaces may be a result of an overestimation process.

Disclosed herein is a method of manufacturing a surgical guide tool for use in total hip replacement surgery on a proximal portion of a femur having a head, a neck extending distally from the head, and a surface region distal the head. In one embodiment, the method include: a) generating medical imaging data associated with the proximal portion of the femur; b) employing the imaging data to generate a three-dimensional computer-generated femur model of the proximal portion of the femur; c) providing a three-dimensional computer-generated implant model; d) providing a three-dimensional computer-generated tool model of at least a portion of at least a surgical guide tool and a surgical guide tool blank; e) superimposing the femur model and implant model; f superimposing the tool model with the superimposed femur model and implant model; g) computer generating manufacturing instructions from data determined from step f; and h) employing the manufacturing instructions at a manufacturing machine to generate the surgical guide tool.

In one version of the embodiment, the surgical guide tool is generated from a surgical guide tool blank. In one version of the embodiment, the implant model includes a shaft portion and a head portion. Superimposing the femur model and implant model may include: causing a center of the head of the implant model to generally coincide with a center of a head of the femur model; and causing the shaft of the implant model to generally align with a shaft of the femur model.

In one version of the embodiment, superimposing the tool model with the superimposed femur model and implant model includes causing the superimposed location of the tool model to generally correspond to a tool position to be employed by a selected surgical approach. In one version of the embodiment, the method further includes providing at least one of a three-dimensional computer generated sphere model and a computer generated rod model and at least one of: superimposing the sphere model with the femur model so a center of the sphere model is caused to generally coincide with a center of a head of the femur model; and superimposing the rod model with the femur model so the rod model is caused to generally align with a shaft of the femur model. Superimposing the femur model and implant model may include at least one of: causing a center of the head of the implant model to generally coincide with the center of the sphere model; and causing the shaft of the implant model to generally align with the rod model.

In one version of the embodiment, the medical imaging data is generated via at least one of MRI and CT. In one version of the embodiment, the manufacturing machine is at least one of a CNC machine and a SLA.

In one version of the embodiment, the method further includes subjecting the medical imaging data to a segmentation process that determines bone contour lines and then adjusting the bone contour lines outward in locations of the bone contour lines corresponding to regions of the proximal portion of the femur that have surface topography that is unlikely to be accurately replicated during at least one of a three-dimensional computer modeling process and generating the tool via the machine. The surface topography may be at least one of highly varied and too small to be manufactured into the tool. The method may further include employing the adjusted bone contour lines to generate the three-dimensional computer-generated femur model of the proximal portion of the femur. The regions of the proximal portion of the femur that have surface topography that is unlikely to be accurately replicated may include at least one of a portion of a tubercle and a portion of a superior intersection between anterior and posterior regions of the neck. The regions of the proximal portion of the femur that have surface topography that is unlikely to be accurately replicated may include at least one of a portion of a trochanteric fossa and a portion of a superior intersection between anterior and posterior regions of the neck. The regions of the proximal portion of the femur that have surface topography that is unlikely to be accurately replicated may include at least one of a portion of a trochanteric fossa and a portion of a posterior greater trochanter near an intertrochanteric crest. The regions of the proximal portion of the femur that have surface topography that is unlikely to be accurately replicated may include at least one of a portion of a trochanteric fossa and a portion of an intertrochanteric crest.

In one version of the embodiment, the data determined from step f includes a resection plane corresponding to a planar surface of a spacer region of the implant model. The data determined from step f may further include a mating surface corresponding to a region of the femur model contacted by the tool model. The mating surface and resection plane may be positionally referenced to each other. The mating surface and resection plane may be respectively used to define an indexing surface and a saw guide in the tool, the indexing surface and saw guide being configured such that, when the indexing surface matingly contacts the proximal femur, the saw guide will be positioned to facilitate a resection of the proximal femur corresponding to a preoperatively planned resection.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2C is a front view of the surgical guide tool of FIG. 2B.

FIG. 2D is a side view of the surgical guide tool of FIG. 2B.

FIG. 2E is a top plan view of the surgical guide tool of FIG. 2B.

DETAILED DESCRIPTION

Figure 1A:
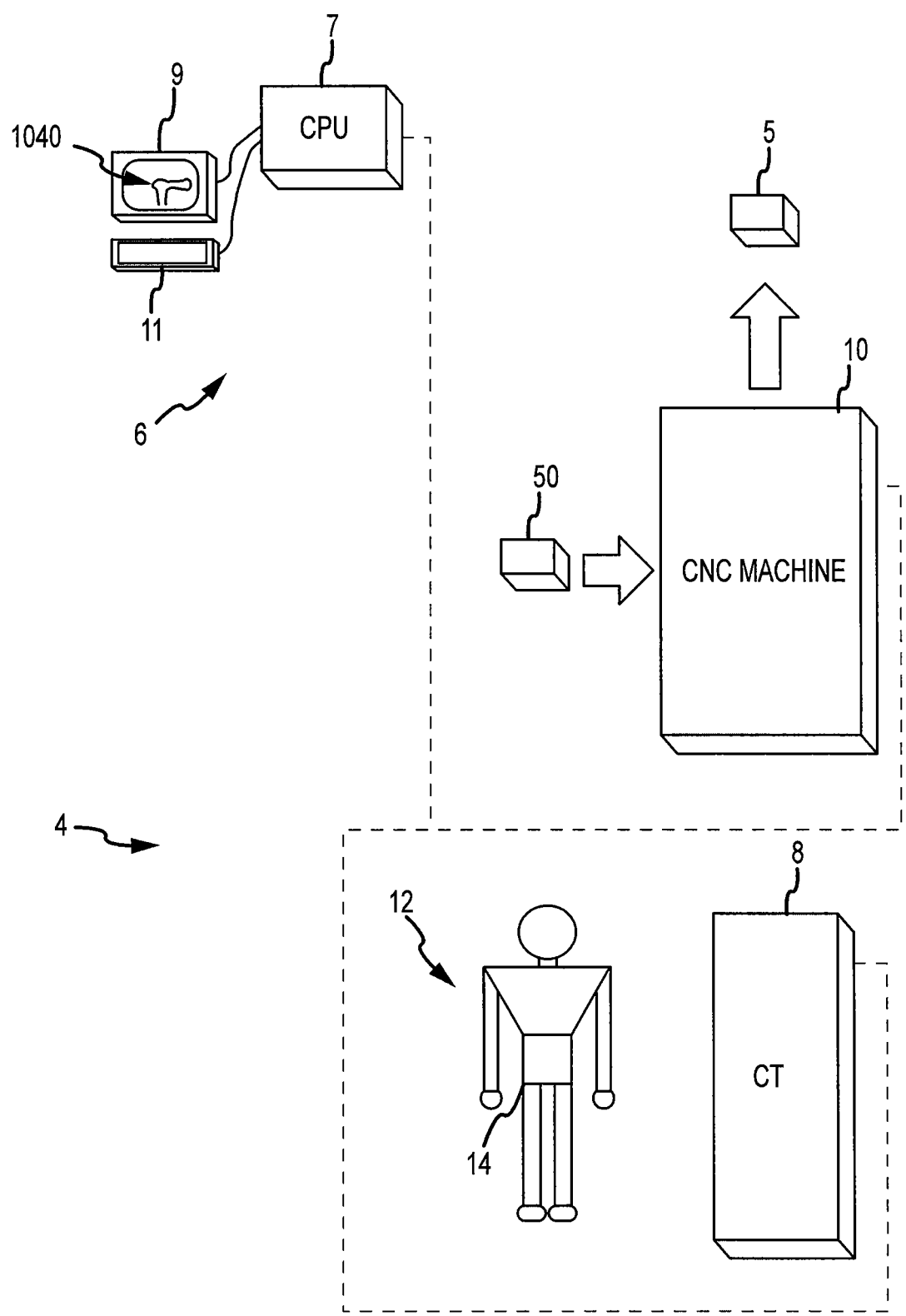
FIG. 1A is a diagrammatic depiction of a system for preoperatively planning and manufacturing a surgical guide tool as described herein.

I. Overview of Tool and its Methods of Planning, Manufacturing and Use

The present disclosure describes a customized surgical guide tool 5 for use in total hip replacement surgery ("THR"). In one embodiment, the customized surgical guide tool 5 may be preoperatively planned via three-dimensional ("3D") computer modeling procedures such that, when the tool 5 is matingly engaged with the proximal femur 40 of the patient, a resection guided by the tool 5 will result in a desired resection that will allow a femoral prosthetic implant or component 800 to be implanted in the femur 40 as planned during the preoperative planning.

In one embodiment, the tool 5 may include a single-piece construction, a fastener receiving feature 1710, a customized saw guide 1725, and a customized indexing or mating region 20 having customized indexing or mating surfaces 708a, 710a. The fastener receiving feature 1710 may be used to receive an anchor that may secure the tool 5 in mating engagement with the proximal femur 40.

The mating region 20 and its mating surfaces 708a, 710a may be configured such that, when the mating region 20 matingly receives therein a region of the proximal femur 40 having predetermined bone surfaces 708, 710, the mating surfaces 708a, 710a of the mating region 20 of the tool 5 will matingly contact the predetermined bone surfaces 708, 710 on the proximal femur 40. The mating region 20 may also include non-contacting surfaces 718a, 720a that correspond to surfaces of proximal femur 40 that are within the region of the femur engaged by the tool mating region 20 and that have surface topography of such variation that it is difficult to accurately scan or computer model or too small to manufacture into the tool mating region. These non-contacting surfaces 718a, 720a of the tool mating region 20 may be the result of an overestimation process during image segmentation and will be spaced apart in a non-contacting fashion from the adjacent femur surfaces when the tool mating region 20 matingly receives the femur 40.

The saw guide 1725 may be a slot, planar surface, or other feature capable of guiding a saw blade during a sawing procedure. The saw guide 1725 may be positioned and oriented relative to the customized mating or indexing region 20 such that, when the mating surfaces 708a, 710a of the mating region 20 matingly contact the bone surfaces 708, 710 when the tool mating region 20 matingly receives therein the region of the femur 40 having the bone surfaces 708, 710, the saw guide 1725 may be oriented over the femur neck 35 such that the saw guide 1725 corresponds with a desired resection plane 805 through the femoral neck 35 that was identified during the preoperative planning. The resection plane 805 may correspond with a spacer region 801 of the femoral prosthetic implant or component 800 that limits the extent to which the femoral component may be inserted into the resected proximal femur during implantation.

When the mating or indexing surfaces 708a, 710a of the mating region 20 of the tool 5 matingly contact the bone surfaces 708, 710 as the mating region 20 mating receives the region of the femur including the bone surfaces 708, 710, a saw extending through the saw slot 1725 will be caused to saw through the femur neck 35 at the desired and preoperatively planned resection plane 805, thereby creating a resected portion of the neck 35 that is configured to receive an implanted femoral component 800 in a manner that replicates the pre-operatively planned implant position and alignment. Once the femur resection is completed with the tool 5 and the femur is further prepped as needed, the femoral component 800, which may be selected based on the information obtained during the preoperative planning, may then be inserted into the resected proximal femur 40.

As stated above, in some embodiments, the tool 5 may have a single-piece construction, which may increase the accuracy associated with the resectioning process by minimizing tolerance errors normally associated with multi-piece, multi-joint, conventional guide tools. In other embodiments, the tool 5 may have a multi-piece construction. For example, the saw slot 1725 may be in the form of a separate guide that is mounted on the rest of the tool 5 in an indexed manner, the rest of the tool 5 having the customized mating region having the customized mating surfaces.

The guide tool 5 aids the surgeon in accurately implanting the femoral component 800 during a THR according to an alignment and position determined during preoperative planning. Specifically, the tool 5, once matingly engaged with the proximal femur, may guide the resection of the proximal femur according to a resection plane identified during the preoperative planning. Accurate implant alignment and position is important because an improperly positioned and aligned femoral component 800 may result in a change of leg length, dislocation of the hip or perforation of the femur.

Furthermore, because the tool 5 is configured to generally automatically provide an appropriate resection through the femur neck for a proper alignment of the femoral component upon causing the indexing region 20 to matingly receive the region of the femur having the bone surfaces 708, 710, the time and effort required by the surgeon to properly prepare the femur for the implantation of the femoral component 800 is substantially minimized. Thus, use of the tool 5 may reduce the overall time spent in surgery. The reduction in the time spent in surgery may reduce the patient's chances of infection.

In some embodiments, a three dimensional ("3D") model of the patient's proximal femur 40 is computer generated from two dimensional ("2D") medical imaging slices 500 (e.g., CT slices, MRI slices, etc.) taken of the patient's proximal femur 40. A sphere 3D computer model 701 and a rod 3D computer model 702 may be respectively aligned with the femoral head 30 and medullary canal 170 or the central axis 100 of the femur shaft of the femur 3D computer model 1040 to approximate the positioning of the femoral component 800 relative to the center of the hip joint 703. A 3D model of the femoral component 800 may be selected from a database of 3D models of candidate femoral component 800. The selected 3D model of the femoral component may be aligned with the 3D model of the femur 40 and the sphere and rod models 701, 702 such that the component head is generally centered with the center of the sphere model and the component shaft is generally coaxial with the rod model.

A 3D model of a blank of the tool 5 may be positioned on the femur model, which is still aligned with the sphere, rod and femoral component models 701, 702, 800. The resection plane may be determined from the location of a spacer region surface or distal end 803 of a spacer region 801 of the femoral component 800 and used to define a saw slot 1725 in the 3D model of the blank of the tool 5. The 3D model of the femur is analyzed to determine shape and location of the mating or indexing femur surfaces 708, 710. The shape and location of the surfaces 708, 710 may be used to define corresponding mating surfaces 708a, 710a in the mating region 20 of the 3D model of the blank of the tool 5. The indexing surfaces 708a, 710a of the mating region 20, the saw slot 1725, and the orientation relationships between the surfaces 708a, 710a and the saw slot 1725 may be imported into the 3D computer generated model of the blank of the tool 5. As the 3D femur model, 3D sphere model, 3D rod model and 3D tool blank model are superimposed relative to each other in the above-described orientation and positioning, the surfaces 708a, 710a and saw slot 1725 end up being defined and imported into the 3D tool blank model such that a resulting tool 5 will position the saw slot 1725 to create the preoperatively planned resection in the femur when the mating surfaces 708a, 710a of the mating region 20 matingly contact the femur surfaces 708, 710 when the mating region 20 matingly receives the region of the femur having the femur surfaces 708, 710. The resulting 3D model of the blank of the tool 5 may be used to generate manufacturing instructions (e.g., machining paths, etc.), which are sent to an automated manufacturing device, such as a CNC machine, a stereolithography apparatus ("SLA"), etc. to mill or otherwise manufacture an actual tool 5 from an actual tool blank 50.

As can be understood from the preceding discussion and as discussed in greater detail below, by superimposing a 3D computer generated model of the patient's proximal femur 40 with the 3D computer generated models of the femoral component 800, sphere, and rod, the proper placement and alignment of the femoral component 800 through the proximal femur 40 can be preoperatively planned with a great degree of accuracy. Also, by superimposing the 3D computer generated model of the blank of the tool 5 with the superimposed 3D computer generated models of the patient's femur 40 and the femoral component 800, the relationships between these models can be analyzed to determine the location and orientation of the saw guide 1725, the location and shape of the indexing surfaces 708a, 710a of the mating region 20, and the positional relationship between the saw guide 1725 and indexing surfaces 708a, 710a, all of which can be imported into the 3D computer generated model of the blank of the tool 5 to define such features into the 3D model of the tool blank.

The resulting 3D computer generated model of the blank of the tool 5 may then be used as manufacturing instructions for the automated manufacture of a customized guide tool 5 having a saw guide 1725 that will result in the preoperatively planned resection of the proximal femur 40 when the tool 5 is matingly engaged with the proximal femur such that the indexing surfaces 708a, 710a mating contact the predetermined femur surfaces 708, 710 when the tool mating region matingly receives the proximal femur 40. Thus, the resulting tool 5 is customized for the specific patient via a preoperative planning process that employs a 3D model of the patient's femur compiled from 2D medical images 500 taken of the patient's femur. The resulting tool 5 includes the "data" physically integrated therein that allows the tool 5 to matingly engage the patient femur 40 and direct the resection of the femur as calculated during the preoperative planning process to facilitate a desired preoperatively planned position and orientation of the implanted femur component 800.

II. Total Hip Replacement Surgical Guide Tool

Figure 2A:
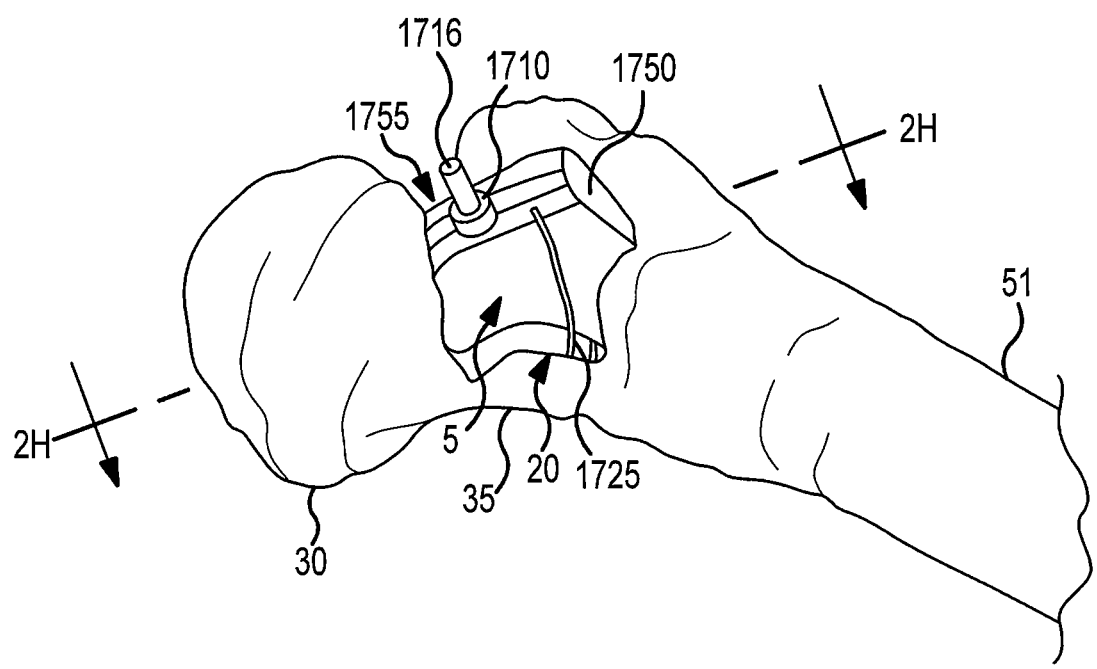
FIG. 2A is an isometric view of a surgical guide tool matingly engaged with a proximal femur having a femoral head and neck.
Figure 2B:
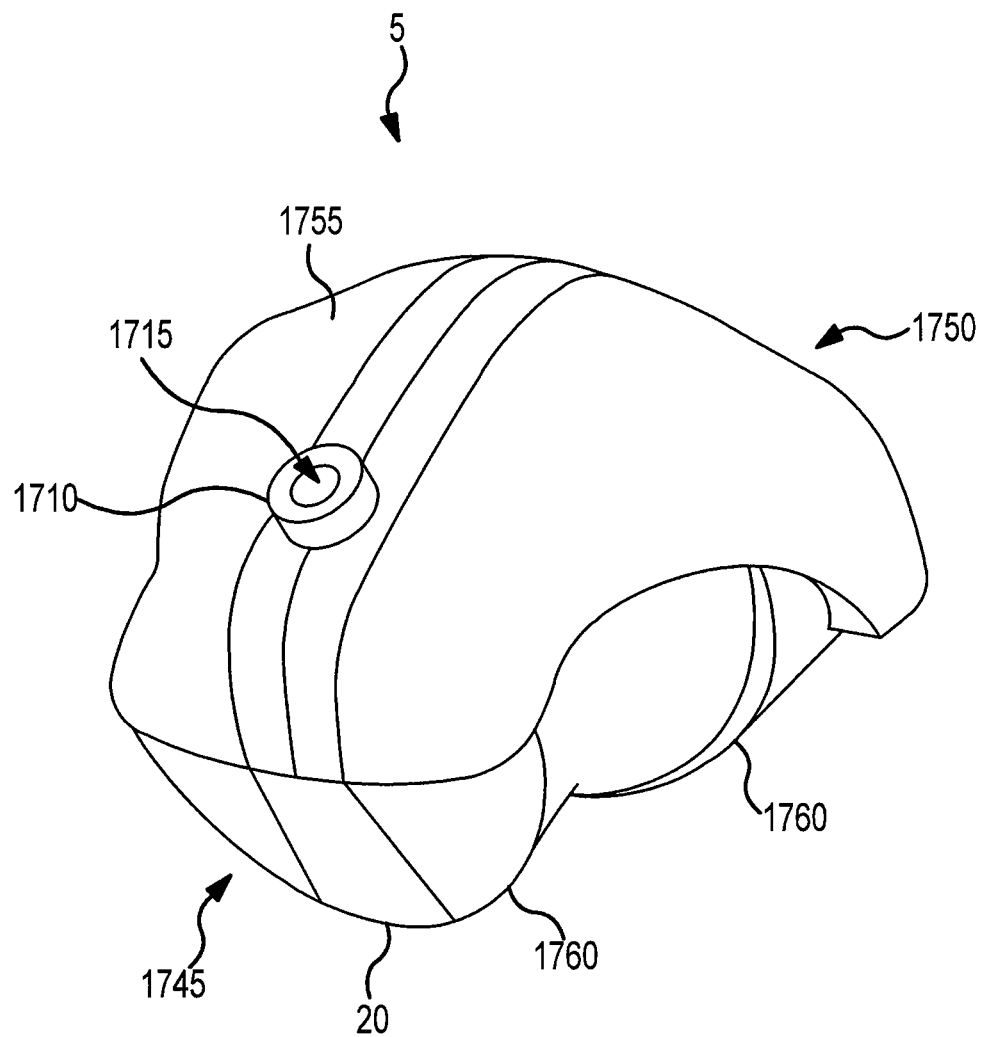
FIG. 2B is a side top isometric view of the surgical guide tool of FIG. 2A, wherein the tool is in a non-customized state or is in the form of a blank from which a customized tool is generated via an automated manufacturing machine, such as, for example, a CNC milling machine.
Figure 2F:
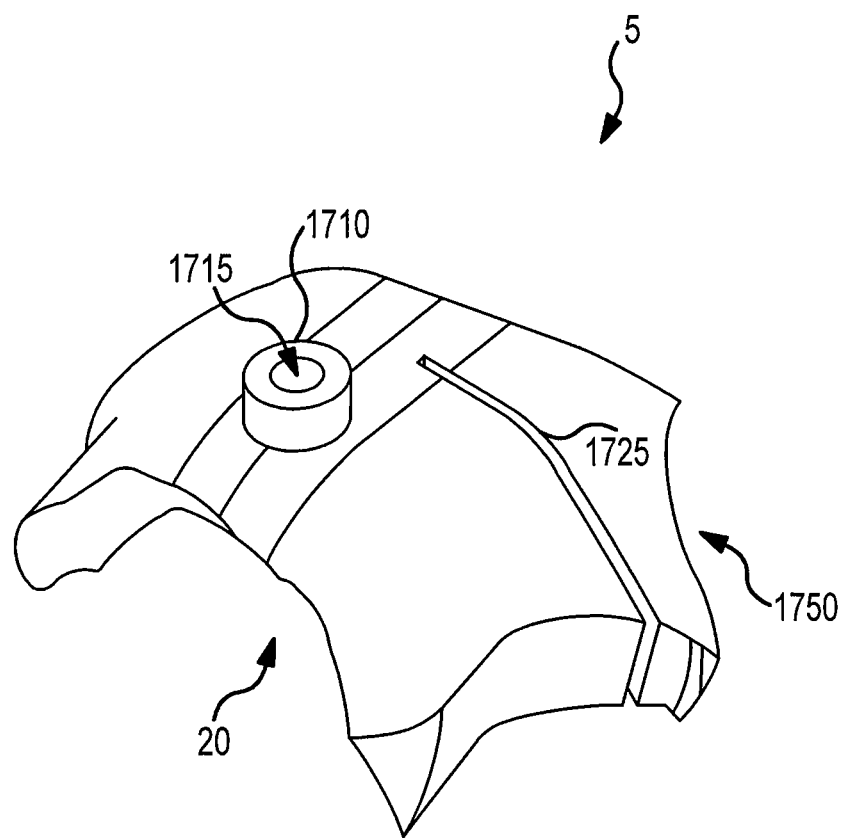
FIG. 2F is the same view as FIG. 2B, except the tool is in the customized state depicted in FIG. 2A and a saw slot is shown.
Figure 2G:
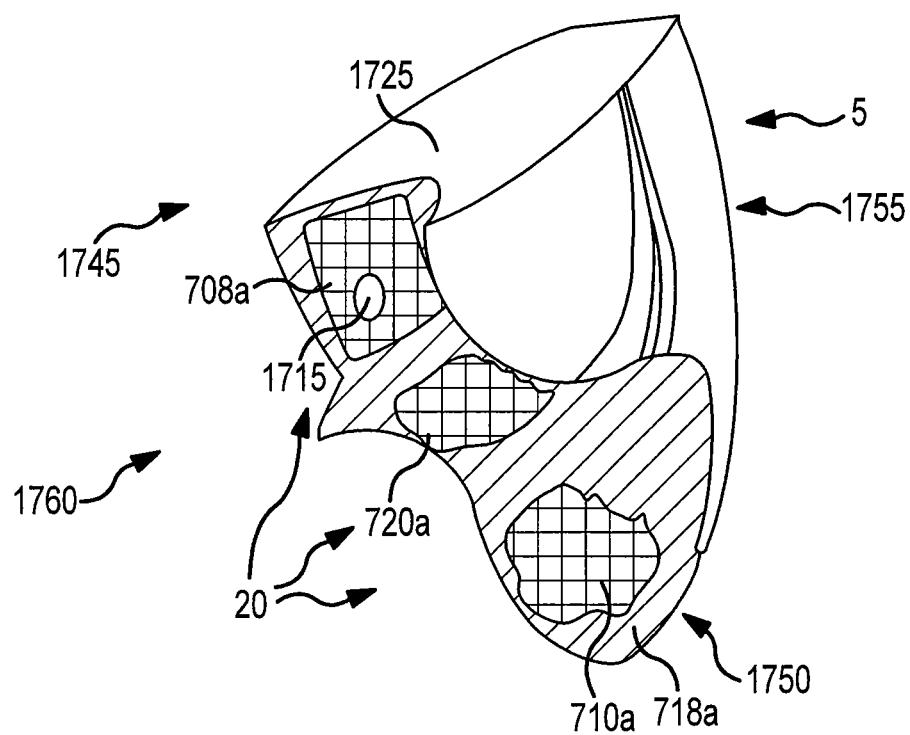
FIG. 2G is a side bottom isometric view of a version of the tool depicted in FIG. 2F, except the tool of FIG. 2G employs a planar surface as the saw guide in place of the saw slot depicted in FIG. 2F, the mating region of the tool of FIG. 2G being configured to engage the mating region of the femur depicted in FIG. 13.
Figure 2H:
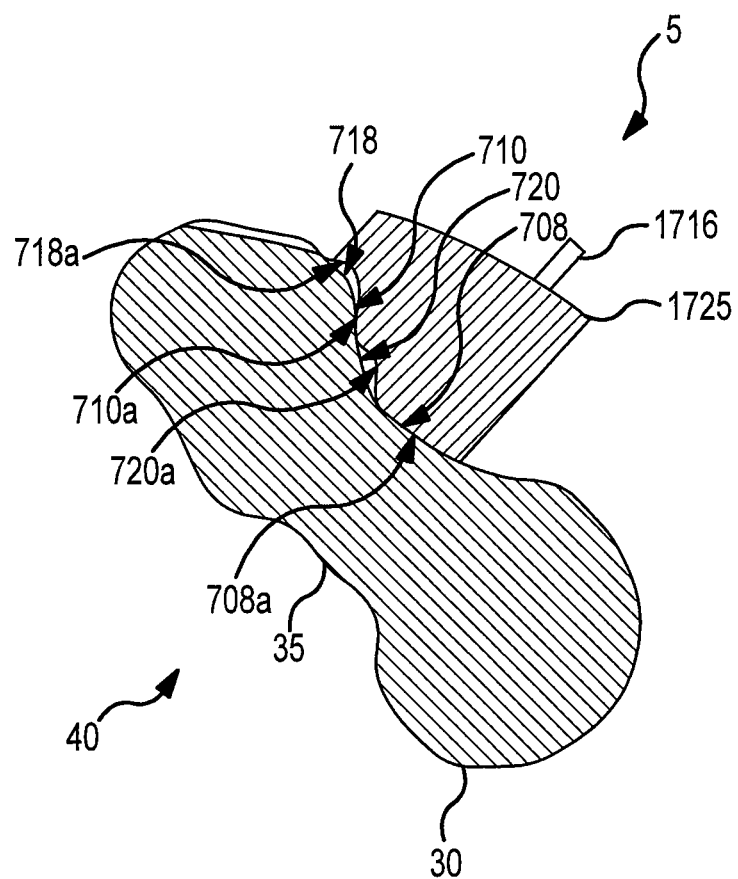
FIG. 2H is a cross section taken through section line 2H-2H, which extends generally posterior-anterior in FIG. 2A, except employing the version of the tool depicted in FIG. 2G.

For a detailed discussion of an embodiment of the surgical guide tool 5 for use in a total hip replacement surgery, reference is made to FIGS. 2A-2H. FIG. 2A is an isometric view of a surgical guide tool 5 matingly engaged on a proximal femur 40 having a femoral head 30 and neck 35. FIG. 2B is a side top isometric view of the surgical guide tool 5 of FIG. 2A, wherein the tool 5 is in a non-customized state or is in the form of a blank from which a customized tool 5 is generated via an automated manufacturing machine, such as, for example, a CNC milling machine. FIGS. 2C-2E are front, side and top plan views, respectively, of the tool 5 of FIG. 2B. FIG. 2F is the same view as FIG. 2B, except the tool 5 is in the customized state depicted in FIG. 2A and a saw slot 1725 is shown. FIG. 2G is a side bottom isometric view of a version of the tool 5 depicted in FIG. 2F, except the tool 5 of FIG. 2G employs a planar surface 1725 as the saw guide 1725 in place of the saw slot 1725 depicted in FIG. 2F, the mating region 20 of the tool 5 of FIG. 2G being configured to engage the mating region of the femur 40 depicted in FIG. 13. FIG. 2H is a cross section taken through section line 2H-2H, which extends generally posterior-anterior in FIG. 2A, except employing the version of the tool 5 depicted in FIG. 2G.

As illustrated in FIGS. 2A-2H, in one embodiment, the surgical guide tool 5 includes a proximal or head end 1745, a distal or greater trochanter end 1750, a top side 1755 and a bottom side 1760. As can be understood from FIGS. 2B-2E, in a non-customized state, the bottom side 1760 and the top side 1755 are generally arcuately shaped. As shown in FIG. 2E, in one embodiment, the width of the tool 5 may gradually increase from the proximal end 1745 to the distal end 1750. The ends 1745, 1750 are formed or otherwise joined together via the bottom side 1760 and top side 1755 such that the tool 5 may be a single-piece tool having a single-piece construction that is generally unitary and continuous in nature. In other embodiments, the tool 5 may have a multi-piece construction, for example, where the saw guide is mounted as a separate and independent piece on the rest of the tool that includes the mating region. The tool 5 may be made of polyoxymethylene (acetal resin), a low density polyethylene, or other biocompatible plastics.

As can be understood from FIGS. 2F-2H, portions of the bottom side 1760 and the top side 1755 may include a customizable mating or indexing region 20 that may have mating contact surfaces 708a, 710a and non-contacting surfaces 718a, 720a defined therein. The mating or indexing region 20 may be adapted to matingly receive regions of the proximal femur 40 having mating contact surfaces 708, 710 and non-contacting surfaces 718, 720 such as those discussed in detail later this Detailed Description with respect to FIG. 13 or similar to those discussed in detail with respect to FIGS. 14A-16B.

For example, as can be understood from FIGS. 2A, 2G, 2H and 13, the region of the femur 40, which may be matingly received by the tool mating region 20 when the tool 5 is mounted on the femur 40, may include a mating contact surface 708 covering portions of the posterior region of the neck 35 and a mating contact surface 710 that is a narrow band following along the intertrochanteric crest 116. Since the tool 5 is customized to fit the patient's specific bone geometry, the mating contact surfaces 708a, 710a of the tool mating region 20 may be configured to matingly contact the mating contact surfaces 708, 710 of the femur 40 when the tool mating region 20 matingly receives therein the region of the femur that has the mating contact surfaces 708, 710. The femur surfaces 708, 710 to be mated or indexed by the tool mating or index surfaces 708a, 710a may be separated by non-contacting surfaces 718, 720 of the femur 40. The non-contacting surfaces 718, 720 of the femur 40 may be spanned in a spaced-apart, non-contacting arrangement by non-contacting surfaces 718a, 720a of the tool mating region 20 when the tool mating region 20 matingly receives the region of the femur 40 including the non-contacting surfaces 718, 720 and the tool mating surfaces 708a, 710a matingly contact the femur contacting surfaces 708, 710. The non-contacting surfaces 718a, 720a of the tool mating region 20 may be the result of an over-estimating process occurring during image segmentation as described later in this Detailed Description. As can be understood from FIG. 13, the non-mating surfaces 718, 720 of the proximal femur 40 may include portions 718 of the posterior greater trochanter 115 and portions 720 of the trochanteric fossa 210 (i.e., the depression between the greater trochanter and the femur neck).

As shown in FIGS. 2B-2E, the top side 1755 may include a fastener-receiving feature 1710. The fastener-receiving feature 1710 may be generally ring shaped and may include a hole 1715 extending axially therethrough. In one embodiment, the top side 1755 includes one fastener-receiving feature 1710. In some embodiments, the top side 1755 includes more than one fastener-receiving feature 1710. The fastener receiving feature 1710 is configured to receive a fastener 1716 through the hole 1715, thereby securing the tool 5 to the femur 40 when the indexing surfaces 708a, 710a of the tool mating region 20 matingly contact the corresponding bone surfaces 708, 710. In some embodiments, the top face does not include a fastener receiving feature 1710 and the tool is secured by other methods, such as being held in place by the surgeon. The fastener 1716 may be a pin, screw or other suitable device.

As can be understood from FIGS. 2F and 2G, in a customized state, the top side 1755 may also include a saw guide 1725 that is configured to receive a saw blade during a THR. The saw guide 1725 may be in the form of a planar surface, a slot or any other feature capable of guiding a saw during a resection. In one embodiment, the saw slot 1725 is generally an open-ended rectangle and extends axially through the tool 5 from the top side 1755 to the bottom side 1760. In some embodiments, the saw slot 1725 may extend across the entire width of the neck 35 such that the surgeon may make a complete resection of the neck. In some embodiments, the saw slot 1725 may extend at least partially across the width of the neck such that the surgeon may make a partial neck resection.

As will be discussed in more detail below with respect to FIG. 12, the saw slot 1725 may be positioned in the tool 5 such that the slot 1725 is aligned with a preoperatively planned resection plane 805, as determined by 3D modeling. The resection plane 805 may correspond with a spacer region 801 of the femoral prosthetic implant or component 800 that limits the extent to which the femoral component may be inserted into the resected proximal femur during implantation. The resection plane 805 defines the location of the head and neck resection during surgery. Thus, when a saw blade is inserted into the saw slot 1725, the subsequent cut through the neck 35 of the proximal femur 40 will expose a portion of the neck 35 for receipt of the femoral component 800. Because the location of the saw slot 1725 is determined based on preoperative planning employing 3D models of the patient's femur and the specific implant 800 to employed in the THR, the subsequent cut through the neck is positioned to expose a portion of the neck aligned to receive the femoral component 800 such that the femoral component 800 may be accurately positioned upon insertion into the femur.

III. System for Planning and Manufacture of Tool

The above-described customized guide tool 5 may be designed and manufactured employing a system 4 similar to that schematically depicted in FIG. 1A. As shown in FIG. 1A, the system 4 may include a preoperative planning system 6 in the form of a computer 6 having a CPU 7, a monitor or screen 9 and operator interface controls 11, such as a keyboard, mouse, etc. The computer 6 may be linked to a medical imaging system 8, such as a CT or MRI machine 8, and an automated or rapid manufacturing machine 10, such as a stereolithography apparatus ("SLA") or a computer numerical controlled ("CNC") milling machine 10. The imaging machine 8, the manufacturing machine 10, and the modeling system 6 of the system 4 may be in communication with each other via, for example, hardwire, internet, wireless, portable memory devices or any combination thereof.

The medical imaging machine 8 may be employed to generate medical images 500 of the joint 14 of the patient 12 that is the subject of the arthroplasty. While this Detailed Description is given in the context of the joint 14 being a hip joint 14 and the tool 5 being configured for the preparation of the proximal femur 40 to receive a total hip replacement prosthetic implant, the concepts disclosed herein may be readily applicable to arthroplasty for other types of joints, including, for example, ankles, knees, wrists, elbows, shoulders, vertebra, fingers, toes, etc. Any resulting 2D medical images 500 may be sent to the computer 6 for use in the preoperative planning.

During preoperative planning, an operator may view the various 3D computer generated models, such as the femur model 1040 and others, via the monitor 11 as the operator interacts with the computer 6 via the controls 11 to direct the preoperative planning. Computer programs for creating, storing and manipulating the various 3D computer generated models may be stored in computer memory accessible by the CPU 7. Computer programs for creating the 3D computer generated bone model 1040 from the 2D images 500 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Once the preoperative planning is completed, the resulting information is used to create manufacturing instructions that are sent to the automated manufacturing machine 10 to generate the final tool 5, which in some embodiments, may be manufactured from a tool blank 50 placed in the manufacturing machine 10.

IV. Medical Imaging, Image Segmentation and Generation of 3D Bone Model

Figure 1B:
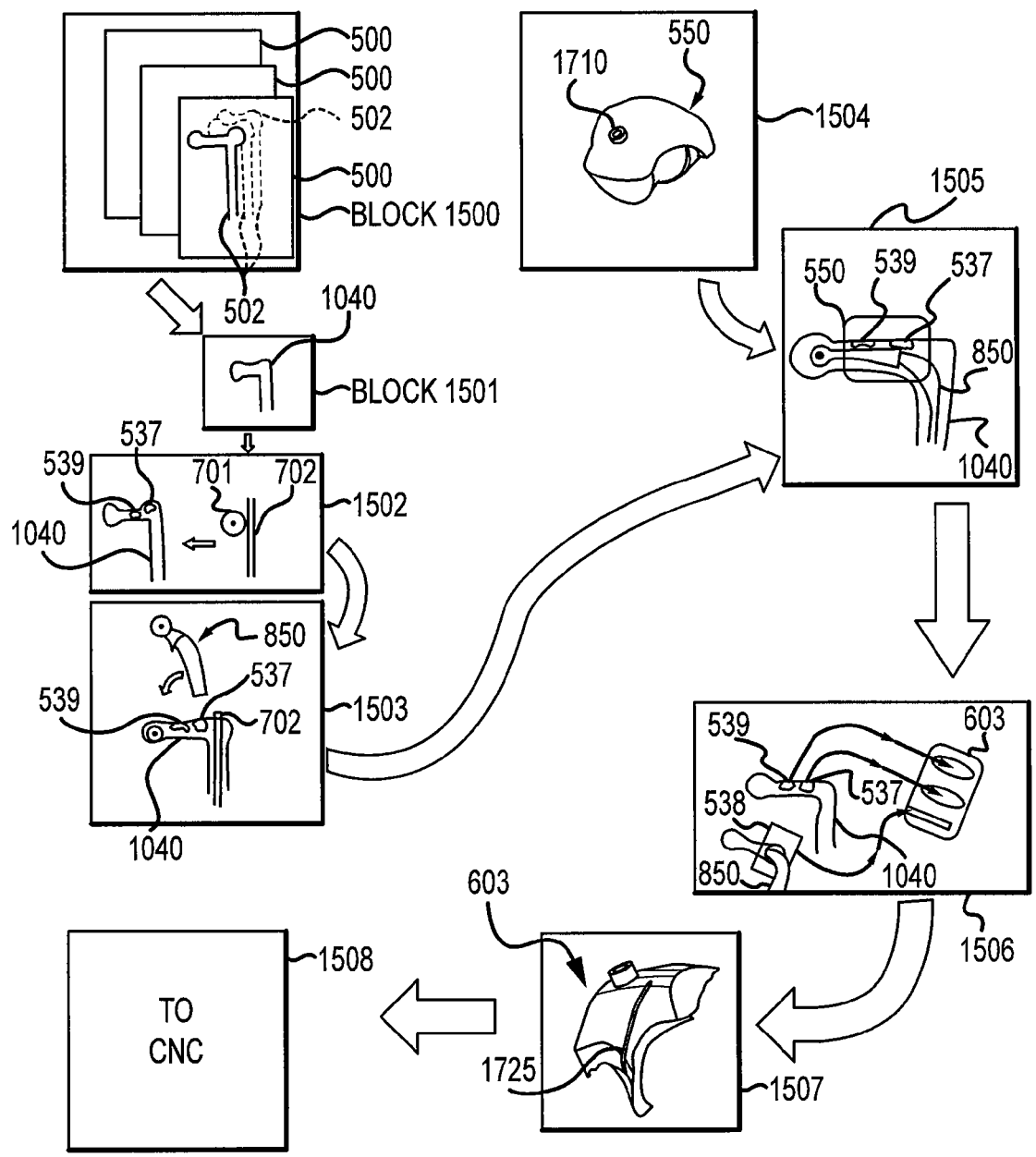
FIG. 1B is a diagrammatic depiction of the preoperative planning process, beginning with the generation of the 2D medical images and ending with the manufacturing instructions being sent to the CNC machine.
Figure 1C:
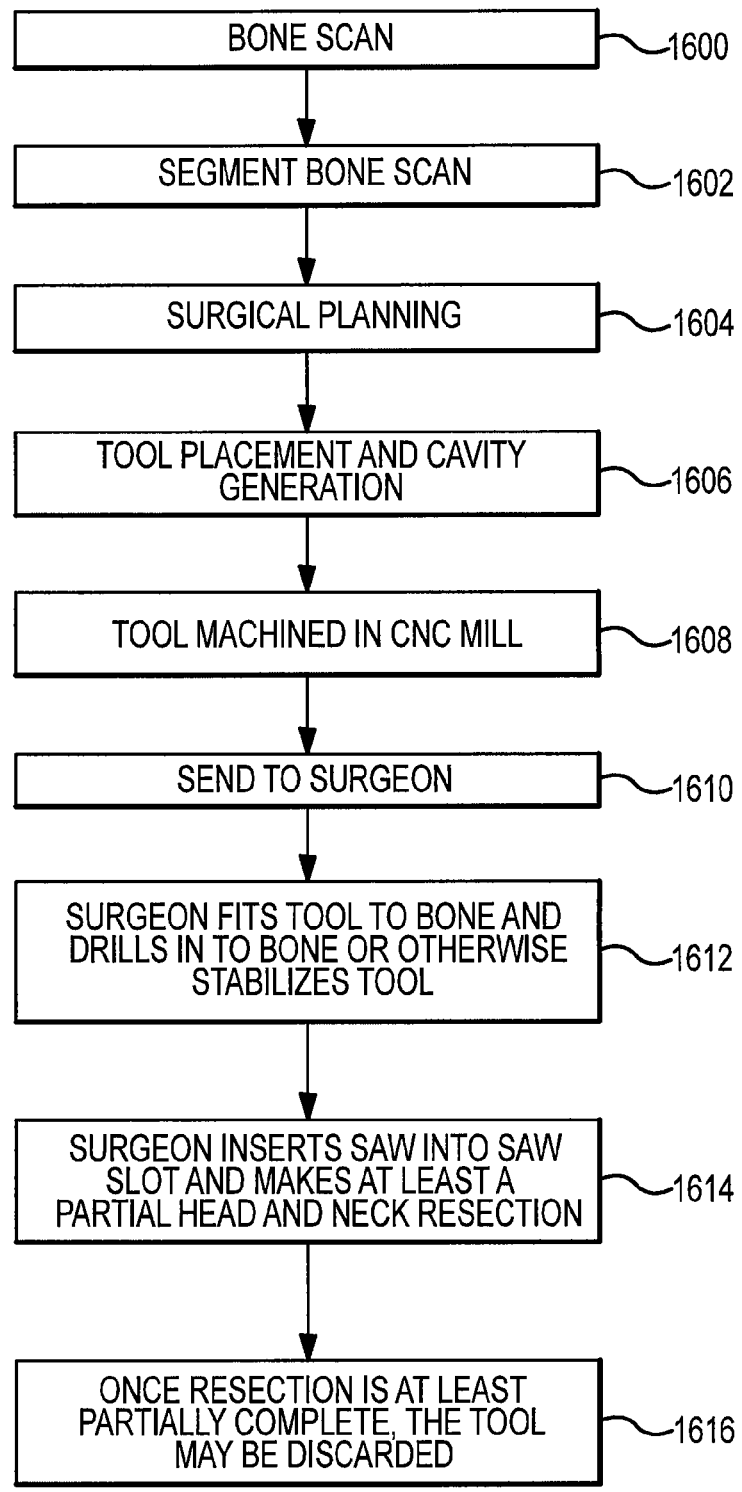
FIG. 1C is a flow chart extending from the generation of the 2D medical images, through the preoperative planning and manufacturing of the tool, and finishing with the tool being employed in the arthroplasty procedure.

For a detailed discussion regarding the medical imaging and image segmentation processes, reference is now made to FIGS. 1A-1C. FIG. 1B is a diagrammatic depiction of the tool planning process, beginning with the generation of the 2D medical images 500 and ending with the manufacturing instructions being sent to the CNC machine 10. FIG. 1C is a flow chart extending from the generation of the 2D medical images 500, through the planning and manufacturing of the tool 5, and finishing with the tool 5 being employed in the arthroplasty procedure.

As indicated in FIGS. 1A-1C, a patient 12 has a hip joint 14 that is the subject of a THR surgery. The hip joint 14 of the patient 12 is scanned in the imaging machine 8 [block 1500 and block 1600]. In one embodiment, the scanning may include up to one-third of the proximal femur 40, including the femoral head 30 and the lesser trochanter 740. In other embodiments, the scanning may include a greater or lesser portion of the femur.

The resolution of a CT scan or an MRI scan is greater than the resolution of x-ray. Greater resolution leads to more accuracy in the preoperative planning process, which leads to greater precision in the resulting tool 5. In some embodiments, the resolution of the scan is between approximately 0 mm and approximately 2 mm. In other embodiments, the resolution of the scan is between approximately 0.3 mm and approximately 0.6 mm. In one embodiment, a CT scan with a resolution of approximately 0.6 mm is utilized for creation of the tool. In one embodiment, a CT scan with a resolution of approximately 0.5 mm to 2 mm, with a tube current ranging from 200 mA to 400 mA and a tube voltage ranging from 120 kV to 140 kV and a direct field of view ("DFOV") ranging from approximately 16 cm to approximately 26 cm is utilized for creation of the tool.

As indicated in FIGS. 1A-1C, in performing the scanning process, the imaging machine 8 makes a plurality of scans of the joint 14, wherein each scan pertains to a thin 2D image slice 500 of the joint 14. The plurality of 2D images 500, which may be CT, MRI or other 2D medical images, are sent from the imaging machine 8 to the preoperative planning system 6. The 2D images are subjected to an image segmentation process, wherein the bone contour lines 502 are identified in each of the images 500 [block 1500 and block 1602].

In one embodiment, the bone surface contour lines of the femur 40 depicted in the image slices 500 may be auto segmented via a image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

Figure 3:
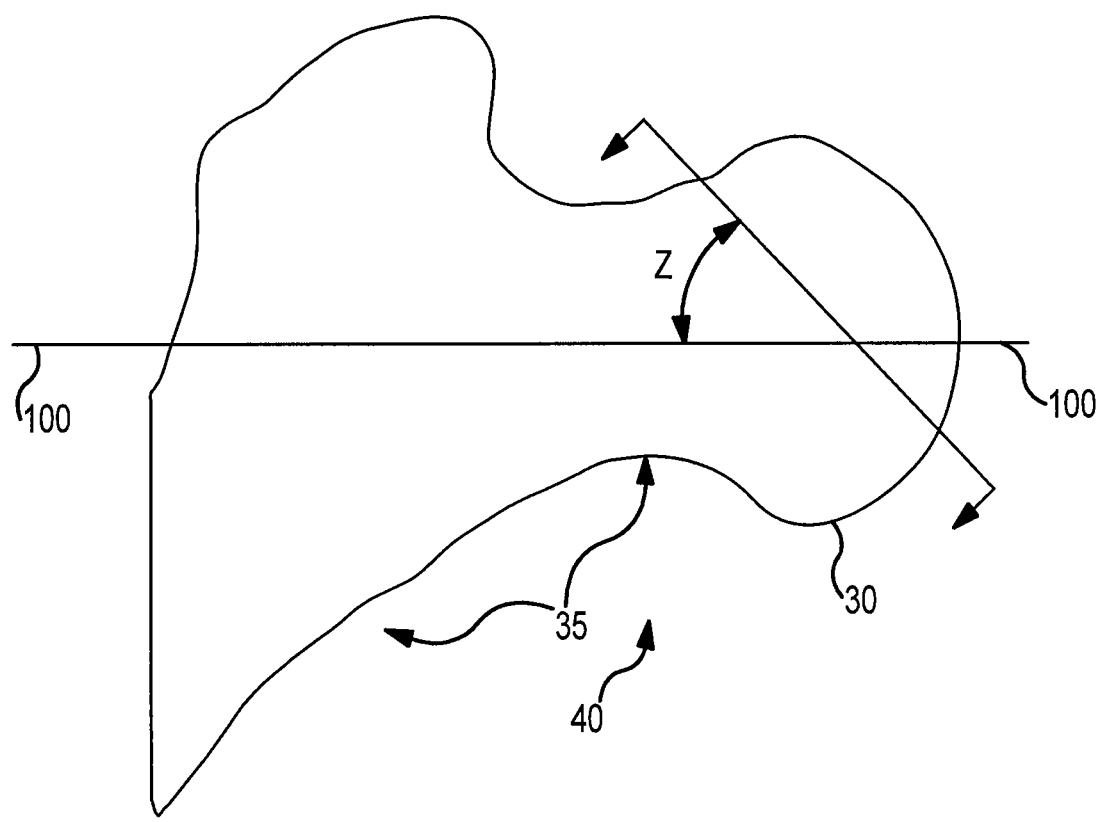
FIG. 3 is a posterior view of a 3D computer generated model of the proximal femur, including its femoral head, neck and greater trochanter, illustrating the angle Z at which the bone scan is sectioned.

As can be understood from FIG. 3, which is a posterior view of a 3D computer generated model of the proximal femur 40, including its femoral head 30, neck 35 and greater trochanter 115, the bone scan may be sectioned for the segmentation process at an angle Z. In other words, in one embodiment, image segmentation is performed utilizing image slices or sections 500 at an angle Z off the central axis 100 of the femoral neck 35 viewed posteriorly. The segmentation can be done in several ways and for ease of the reader are described in relation to a CT-scan. For example, the during the CT scanning of the femur, the CT locator could be positioned at an angle Z to section the CT scan. Alternatively or additionally, the CT scan could be sectioned at an angle Z during post-processing. In one embodiment, the angle Z is between approximately thirty degrees and approximately sixty degrees. In an alternative embodiment, the angle Z is approximately a 45 degree angle. It can be appreciated that segmentation of an MRI scan may be achieved in a similar manner.

Figure 4A:
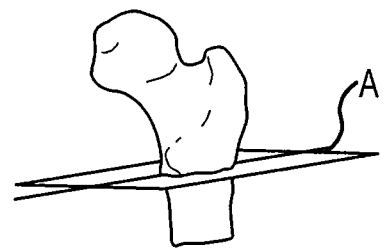
FIG. 4A is a 3D view of the proximal femur of FIG. 2A, illustrating a section line A at which the bone is sectioned during a CT scan to help create a cortical bone model and trabecular bone model.
Figure 4B:
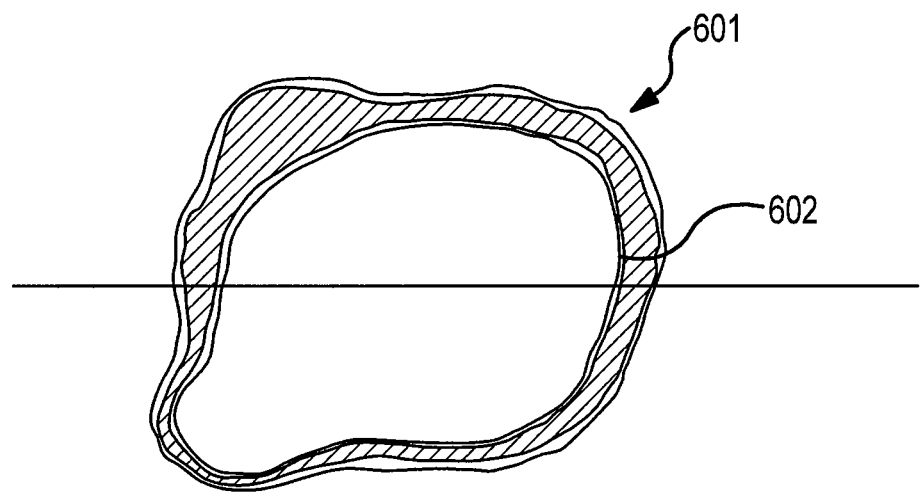
FIG. 4B is a CT slice as taken along section line A of FIG. 2A.
Figure 5A:
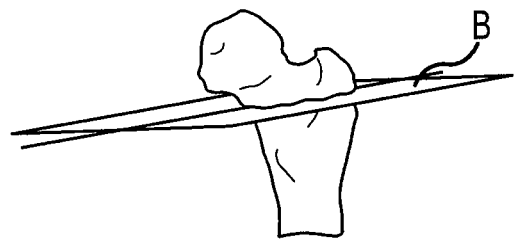
FIG. 5A is a 3D view of the proximal femur of FIG. 2A, illustrating a section line B at which the bone is sectioned during a CT scan to help create a cortical bone model and trabecular bone model.
Figure 5B:
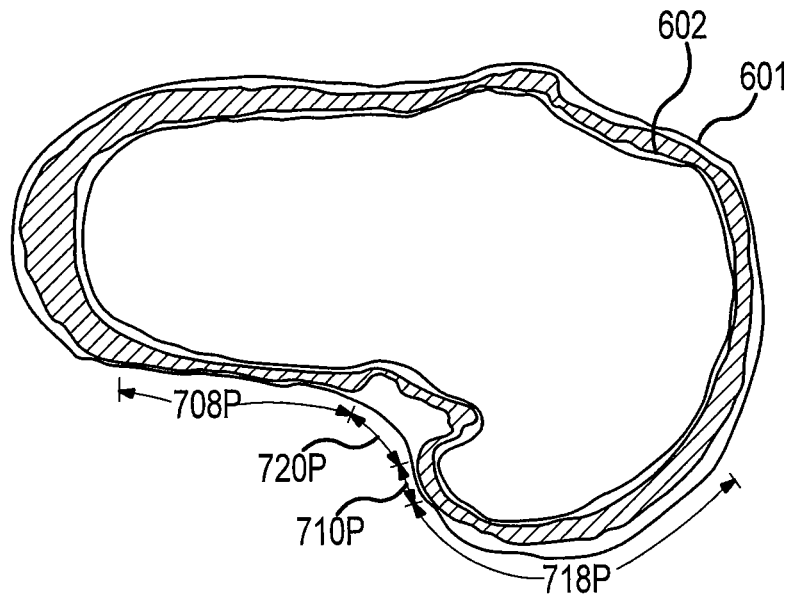
FIG. 5B is a CT slice as taken along section line B of FIG. 5A.
Figure 6A:
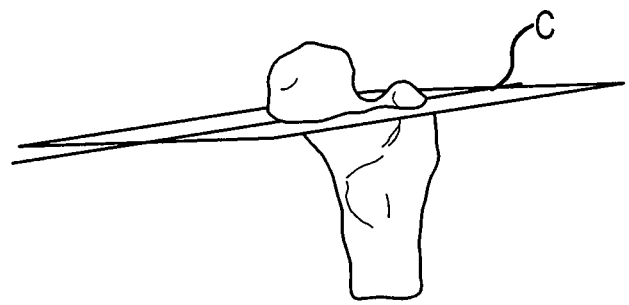
FIG. 6A is a 3D view of the proximal femur of FIG. 2A, illustrating a section line C at which the bone is sectioned during a CT scan to help create a cortical bone model and trabecular bone model.
Figure 6B:
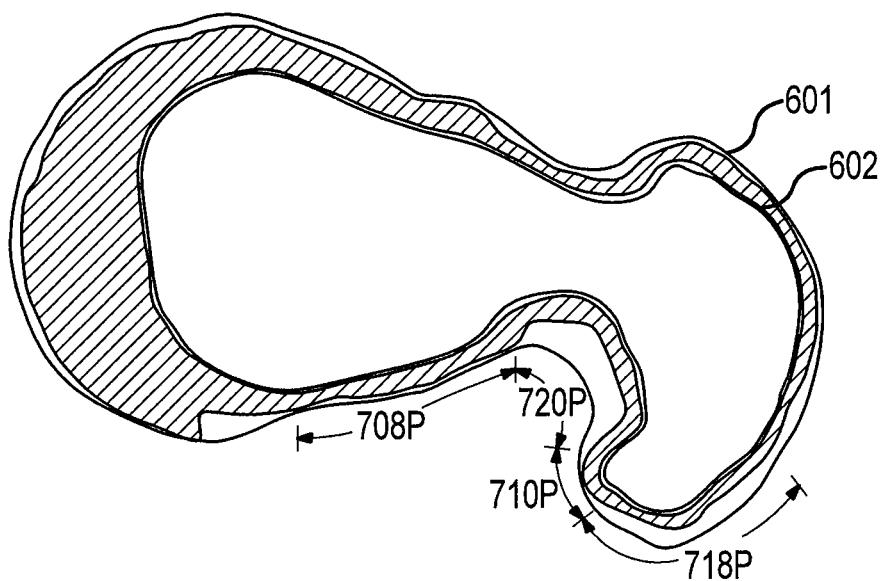
FIG. 6B is a CT slice as taken along section line C of FIG. 6A.

For a discussion of the bone contour lines that may be identified during the image segmentation process, reference is made to FIGS. 4A-6B. FIGS. 4A, 5A and 6A are 3D views of the proximal femur 40 respectively showing section or scan planes A, B and C extending through the femur 40. FIGS. 4B, 5B and 6B are respectively the segmented image slices of planes A, B and C, respectively. As indicated in FIG. 4A, section or scan plane A extends through the proximal femur generally transverse to the femoral axis and just distal of the lesser trochanter. As shown in the resulting segmented image slice depicted in FIG. 4B, the contour line 601 corresponding to the cortical bone and the contour line 602 corresponding to the trabecular bone 602 may be identified.

As indicated in FIG. 5A, section or scan plane B extends through the proximal femur generally transverse to the femoral axis and approximately midway between the tip of the greater trochanter and the lesser trochanter. As shown in the resulting segmented image slice depicted in FIG. 5B, the contour line 601 corresponding to the cortical bone and the contour line 602 corresponding to the trabecular bone 602 may be identified.

As indicated in FIG. 6A, section or scan plane C extends through the proximal femur generally transverse to the femoral axis and just distal the tip of the greater trochanter. As shown in the resulting segmented image slice depicted in FIG. 6B, the contour line 601 corresponding to the cortical bone and the contour line 602 corresponding to the trabecular bone 602 may be identified.

Figure 13:
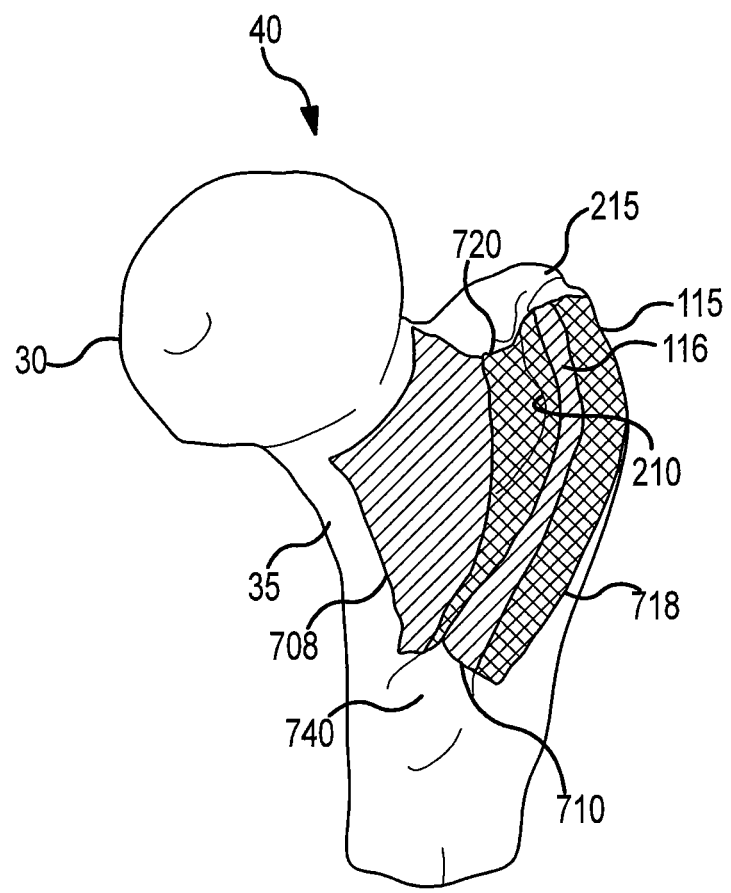
FIG. 13 is a posterior medial view of the proximal femur of FIG. 2A showing the regions of the femur that are mated with the index surfaces of an embodiment of the tool and the regions that correspond to over-estimated or non-contacting surfaces of the tool.

In one embodiment, as can be understood from FIG. 13, the region of the femur 40, which may be matingly received by the tool mating region 20 when the tool 5 is mounted on the femur 40, may include a mating contact surface 708 covering portions of the posterior region of the neck 35 and a mating contact surface 710 that is a narrow band following along the intertrochanteric crest 116. The femur mating contact surfaces 708, 710 may be separated by non-contacting surfaces 718, 720 of the femur 40. The non-contacting surfaces 718, 720 of the proximal femur 40 may include portions 718 of the posterior greater trochanter 115 and portions 720 of the trochanteric fossa 210.

As can be understood from FIGS. 5A, 6A and 13, the portions 708P, 710P of the cortical bone contour lines 601 in FIGS. 5B and 6B correspond to the mating contact surfaces 708, 710 of the femur 40, and the portions 718P, 720P of the cortical bone contour lines 601 in FIGS. 5B and 6B correspond to the non-contact surfaces 718, 720 of the femur 40. As can be understood from FIGS. 4A and 13, the cortical contour line 601 depicted in FIG. 4B is from a slice that would be located below the tool mating regions of the femur 40. Therefore, this contour line 601 depicted in FIG. 4B does not have portions 718P, 720P, 708P, 710P.

As can be understood from FIGS. 5B, 6B and 13, the non-contact portions 718P, 720P of the cortical bone contour lines 601 correspond to surfaces 718, 720 of the femur 40 that are difficult to replicate in the tool mating region 20 due to the extreme variance in surface topography for the surfaces 718, 720. In addition to the difficult to replicate surfaces 718, 720 depicted in FIG. 13, other difficult to replicate surfaces that surfaces portions 718P, 720P may correspond to may include surfaces of osteophytes or other bone surface irregularities. The surface topography variance for the surfaces 718, 720, the osteophytes, etc. may be such that: (1) corresponding regions of the tool mating region 20 would be difficult to machine to correspond to the surfaces 718, 720 of the femur 40 due to limitations in the milling process; or (2) the surfaces 718, 720 would be difficult to model because of limitations in the scanning or 3D computer modeling processes.

The difficult to replicate contour line portions 718P, 720P may be subjected to an overestimation process. Specifically, the difficult to replicate contour line portions 718P, 720P are modified to be extended outwardly away from the interior of the bone (i.e., over-estimated) and, in some instances smoothed with respect to shape. The resulting cortical bone contour lines 601 now include the original portions 708P, 710P in their original shape and location and the now overestimated or outwardly adjusted portions 718P, 720P; these resulting cortical bone contour lines 601 from each image slice are then compiled or reconstructed into the 3D computer generated femur model 1040 used for the preoperative planning process.

The end result of the overestimation process with respect to the manufacture of the completed tool 5 is that the CNC tool paths corresponding to the overestimated regions of the femur model 1040 remove excess materials from the mating region 20 of the blank used to form the tool 5. Accordingly, the tool mating region 20 is configured to matingly contact only with those surfaces 708, 710 of the femur that can be accurately replicated in the tool mating region 20, and those surfaces 718, 720 that cannot be accurately replicated in the tool mating region 20 are not contacted by any surface of the tool mating region 20 because the tool mating region 20 has been over-milled in the areas of the tool mating region 20 corresponding to the difficult to replicate femur surfaces 718, 720. The result is a tool 5 with a mating region 20 that accurately mates to the mating region of the femur 40.

Figure 9A:
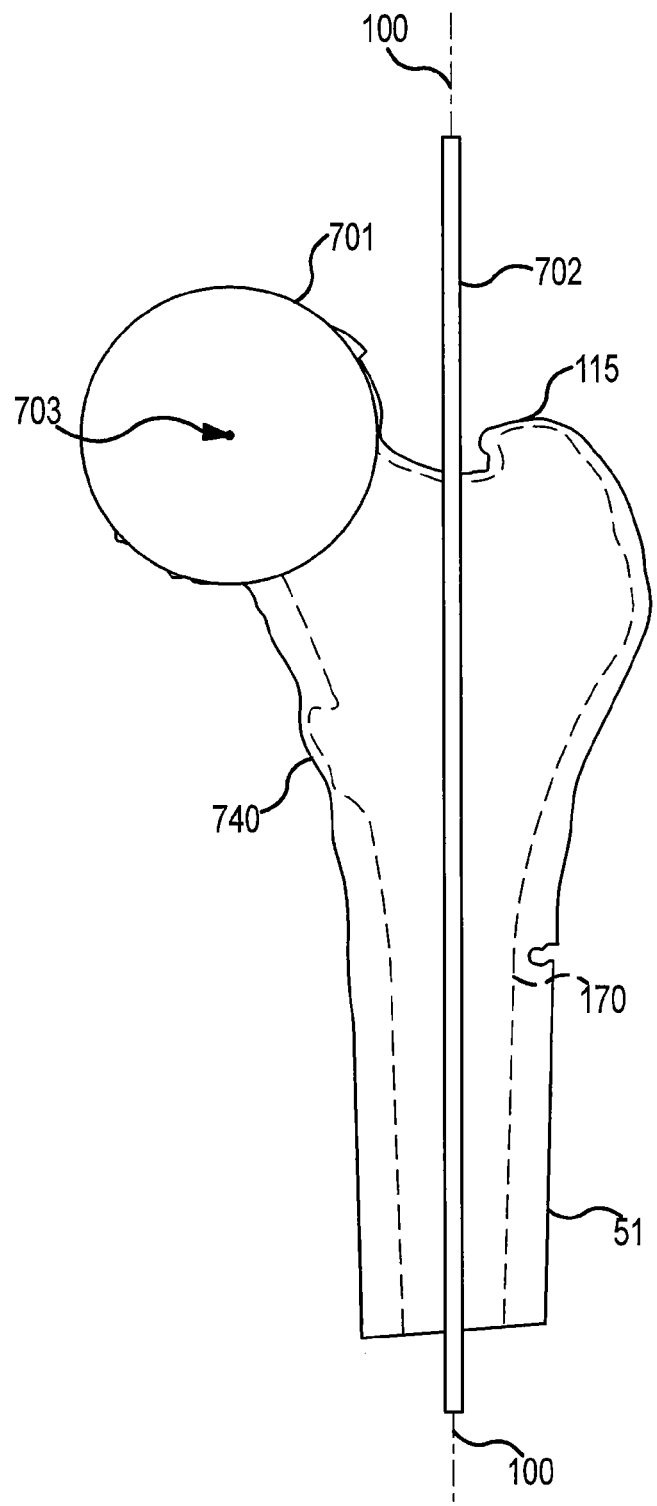
FIG. 9A is a transparent posterior view of a model of the proximal femur of FIG. 2A, wherein a sphere model and a rod model are shown.

In the above-described overestimation process, the line contours 601 for the cortical bone may be subjected to overestimation while the line contours 602 for the trabecular bone are not subjected to overestimation. However, in other embodiments, the contour lines 601, 602 for both the cortical and trabecular bones are subjected to overestimation. The cortical bone contour lines 601 may be employed to generate a 3D computer generated cortical bone model, and the trabecular bone contour lines 602 may be employed to generate a 3D computer generated trabecular bone model. The cortical bone model and the trabecular bone model may be combined into a single 3D computer generated femur model 1040 [block 1501], as depicted in FIG. 9A discussed below. Specifically, as can be understood from FIG. 9A, which is a posterior view of the femur model 1040, once the contour lines are segmented and overestimated as described above, the contour lines may be imported into a 3D computer modeling program. The model program may then be used to generate 3D computer models of the cortical bone 601 and the trabecular bone 602 of the proximal femur 40. The model of the trabecular bone 602 may be subtracted from the model of the cortical bone 601 to create a hollow 3D computer generated femur model 1040, wherein the subtracted model of the trabecular bone 602 creates a hollow region of the femur model 1040 that represents the medullary canal 170.

Overestimation processes are described in more detail in commonly-owned U.S. Patent Application No. 61/083,053, entitled System and Method for Manufacturing Arthroplasty Jigs Having Improved Mating Accuracy, filed Jul. 23, 2008, which is hereby incorporated by reference in its entirety.

Figure 7:
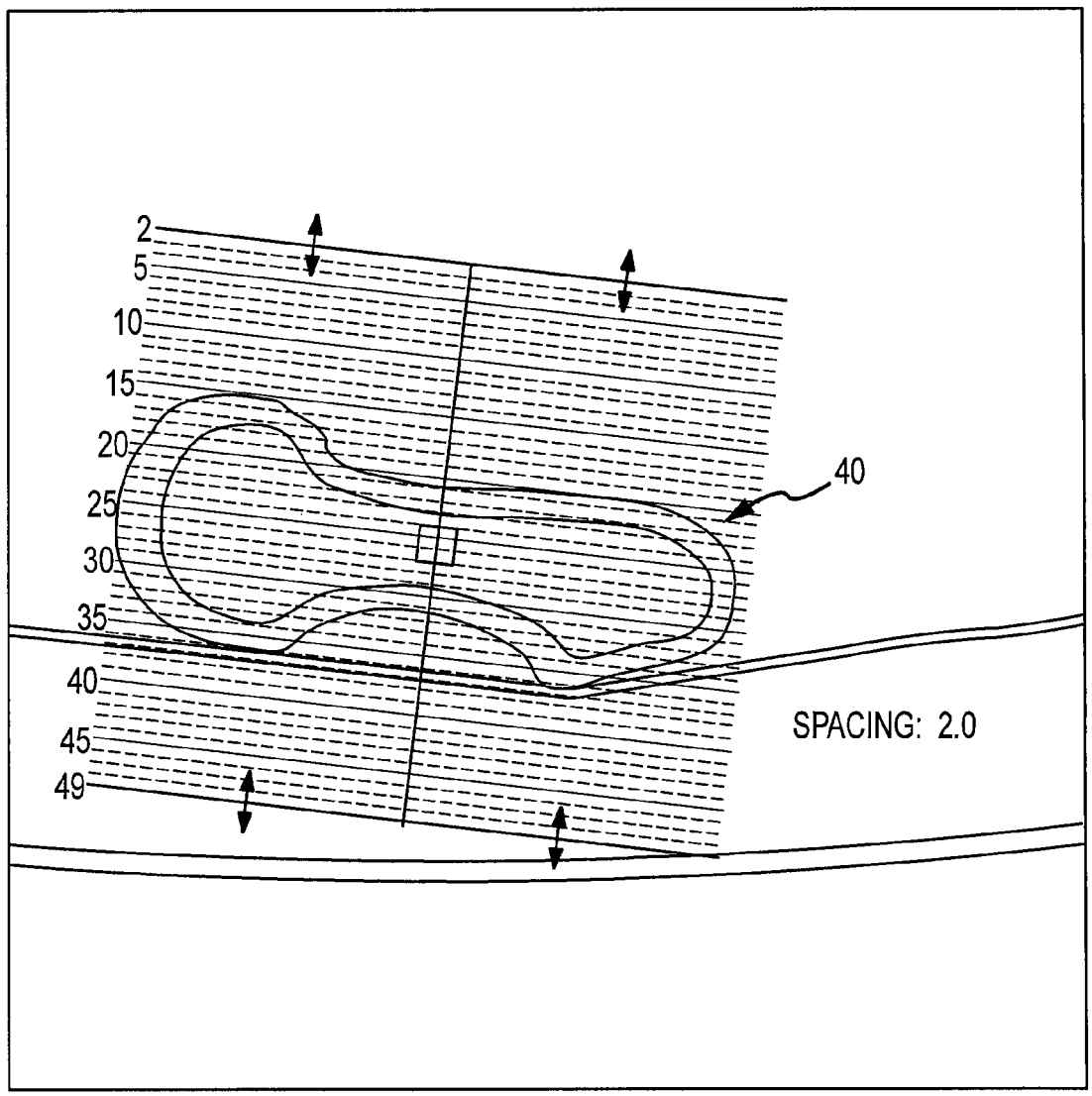
FIG. 7 is an example superior view CT scan of the proximal femur, wherein the correct coronal alignment for CT reconstruction is shown.

When reconstructing the contour lines into the femur model 1040, certain alignments have been found to be advantageous. For example, as indicated in FIG. 7, which is an example superior view CT scan of the proximal femur 40 of FIG. 2A, the CT scan may be reconstructed for proper coronal alignment by causing the coronal slices to be parallel to the femoral neck 35. For this procedure, the slice width and overlap may range from approximately 0.5 mm to approximately 2 mm. In one embodiment, a slice width and overlap of 0.5 mm is used. The DFOV may range between approximately 16 cm to approximately 26 cm field of view. In one embodiment, the reformatted CT scan may include up to one-third of the proximal femur 40, including the femoral head 30 and the lesser trochanter 740. In other embodiments, the CT scan may include a greater or lesser amount of the proximal femur.

Figure 8:
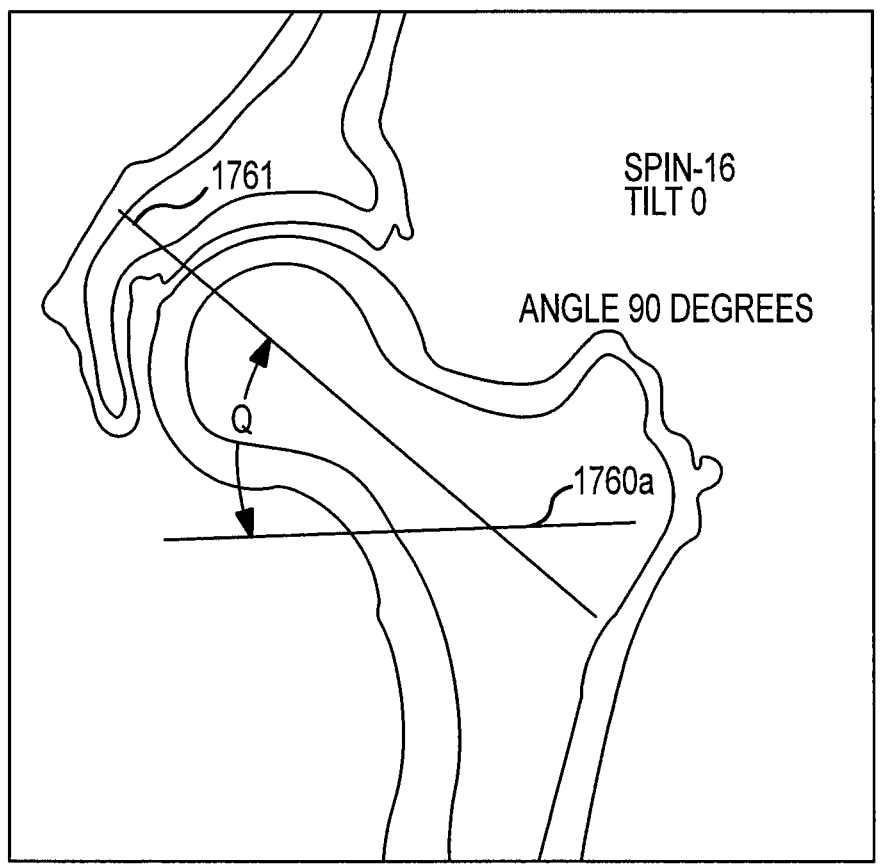
FIG. 8 is an example CT scan of the proximal femur, wherein the correct alignment for the final CT reconstruction is shown.

As indicated in FIG. 8, which is an example CT scan of the proximal femur 40 of FIG. 2A, wherein the proper alignment for the final CT reconstruction is shown from a coronal slice. Specifically, the final reconstruction alignment 1760a is set to an angle Q relative to the long axis 1761 of the femoral neck 35. Angle Q may range from approximately 30 degrees to approximately 60 degrees. In one embodiment, angle Q is 45 degrees. The slice width and overlap may range from approximately 0.5 mm to approximately 2 mm. In one embodiment, the slice width and overlap is 1 mm. The field of view may range from approximately 16 mm to approximately 26 mm. In one embodiment, the scan may include up to one-third of the proximal femur 40, including the femoral head 30 and the lesser trochanter 740. In other embodiments, the CT scan may include a greater or lesser amount of the proximal femur.

V. Preoperative Planning of Tool

As can be understood from FIGS. 1A-1C and the immediately preceding discussion, once the medical images 500 are segmented to identify the bone contour lines 502 [block 1500 and block 1602], the contour lines are overestimated as necessary, and the contour lines are compiled or reconstructed into a 3D model of the femur via a computer modeling program [block 1501], the pre-operative planning process may begin [block 1604], wherein the 3D bone model is utilized to determine: (1) the proper size and placement of a femoral component (e.g. the prosthetic device that will be implanted in the femur); and (2) the location of the resection plane for resection of the femur head and neck, wherein the resection is made to allow for the implantation of the femoral component in the resected femur. The following preoperative planning methods may employ a 3D computer modeling program, such as, for example, Solidworks or Paraview, in the generation, placement, manipulation, determination and importation of various 3D computer models described below.

Figure 9B:
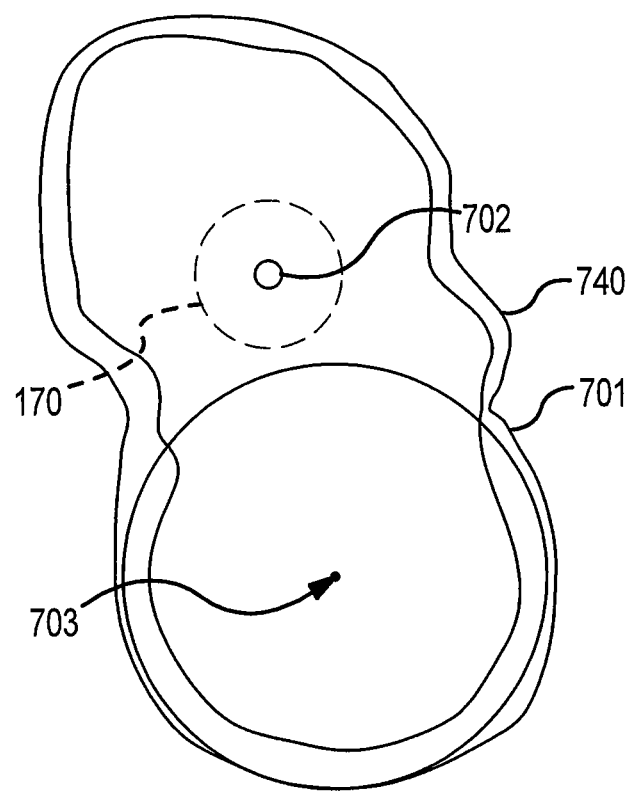
FIG. 9B is a transparent superior view of the models depicted in FIG. 9A.

As can be understood from FIG. 1B and FIGS. 9A and 9B, which are respective transparent posterior and superior views of a 3D computer generated model 1040 of the proximal femur 40 of FIG. 2A, in one embodiment, the preoperative planning may begin with the femur model 1040, a 3D computer generated sphere model 701, and a 3D computer generated rod model 702 being imported into a modeling space [block 1502]. As can be understood from FIGS. 9A and 9B, the femur model 1040, which is a result of the compiled or reconstructed contour lines, some of which may have been overestimated, may have a head 30, a neck 35, a shaft 51, a greater trochanter, and an medullary canal 170.

As indicated in FIGS. 9A and 9B, the models 701, 702, 1040 are combined together in a superpositioned arrangement. Specifically, the rod model 702 may be positioned so that it generally aligns with the center of the medullary canal 170 of the shaft of the femur model 1040, which generally corresponds to a central axis 100 of the shaft of the femur. In other words, the rod 702 may be positioned to be generally coaxial with the femur axis 100.

The sphere model 701 may be positioned so the centers of the sphere 701 and head 35 are located at the same point. The diameter of the sphere model 701 may be increase or decreased to cause the sphere model 701 to generally approximate the femoral head 30 such that the hemispherical surfaces of the head 30 and the sphere 701 are generally coextensive for a significant portion of the hemispherical surface of the head 30. Generally, if there is damage to the head 30, the damage is typically to the superior and anterior surfaces, so the sphere 701 is typically positioned and sized such that hemispherical surface of the sphere 701 is generally coextensive with the inferior and posterior regions of the head 30. Once the sphere 701 is properly placed and sized, the center 703 of the sphere 701 will generally approximate the center of the hip joint. The proper positioning and sizing of the models 701, 702 can be verified by looking at both posterior (FIG. 9A) and superior (FIG. 9B) views.

Figure 9C:
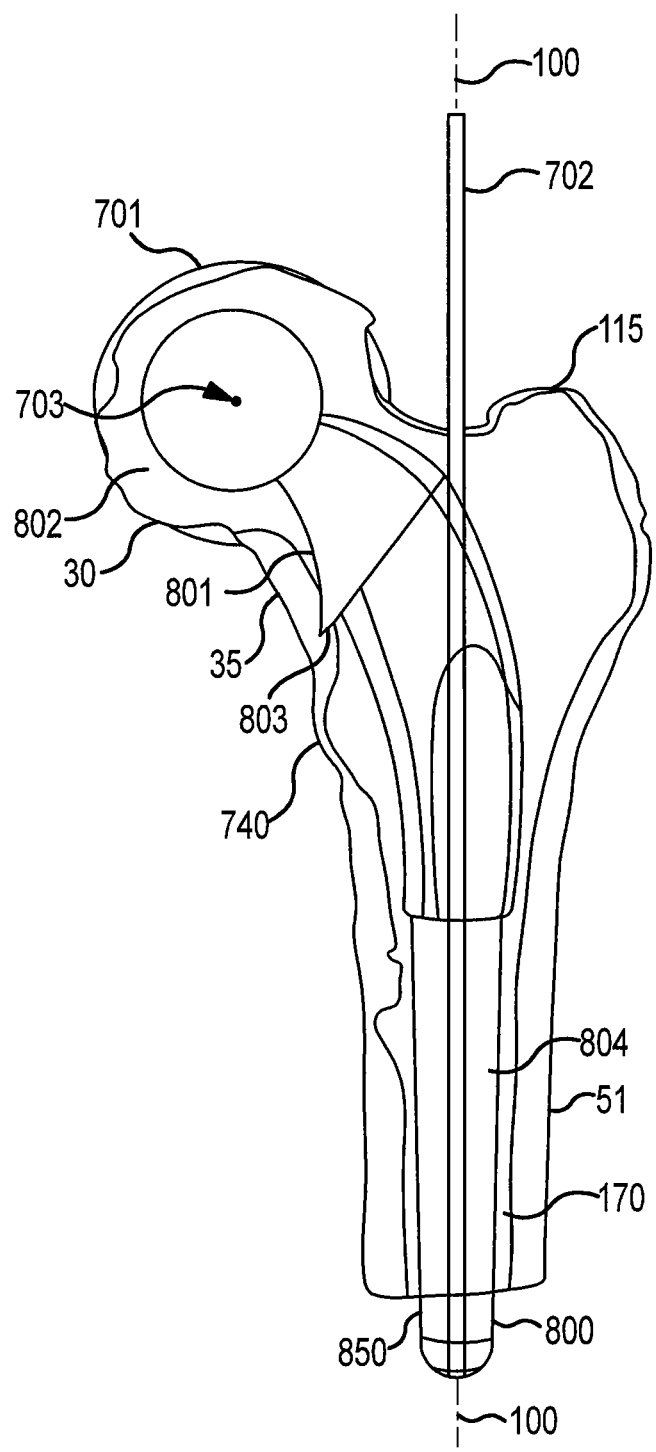
FIG. 9C is the same view as FIG. 9A, except a femoral component model is also shown.

As can be understood from FIG. 1B and FIG. 9C, which is the same view as FIG. 9B, except with a femoral component model 850 depicted with the other models 701, 702, 1040, a 3D computer generated femoral component model 850 may be imported into the modeling space [block 1503]. The femoral component model 850 may include a shaft 804, a head 802 and a spacer region 801. The spacer region 801 may have a surface 803 that abuts against the surface of the bone resection when the actual implant is properly and fully implanted in the resected femur. The 3D femoral component model 850 may be selected from a database of femoral component models, the models in the data base corresponding to the sizes of femoral components available from a selected manufacturer. Size selection is based on the shape and size of the medullary canal 170. Once the position of the neck resection has been determined, the largest component that fits within the canal is chosen.

The sphere model 701 and rod model 702 are used to plan the proper alignment and placement of the femoral component model 850. Specifically, the femoral component model 850 may be superimposed with the rest of the models 701, 702, 1040 such that the long axis of the shaft 804 of the component 800 generally corresponds to the long axis of the rod 702 in a generally coaxial manner, and the center of the head 802 of the component model 850 generally corresponds to the approximated hip joint center 703. To properly position the component model 850, the size and the shaft to neck angle of the spacer 801 may be adjusted according to the ranges available from the manufacturer for the femoral component.

The above-described embodiment superimposes the sphere and rod models 701, 702 on the femur model 1040 prior to superimposing the femoral component model 850 and using the sphere and rod model locations to position and size the femoral component model 850. However, in other embodiments, the femoral component model 850 may be superimposed on the femur model 1040 for positioning and sizing without the presence and use of the sphere and rod models 701, 702.

Figure 10:
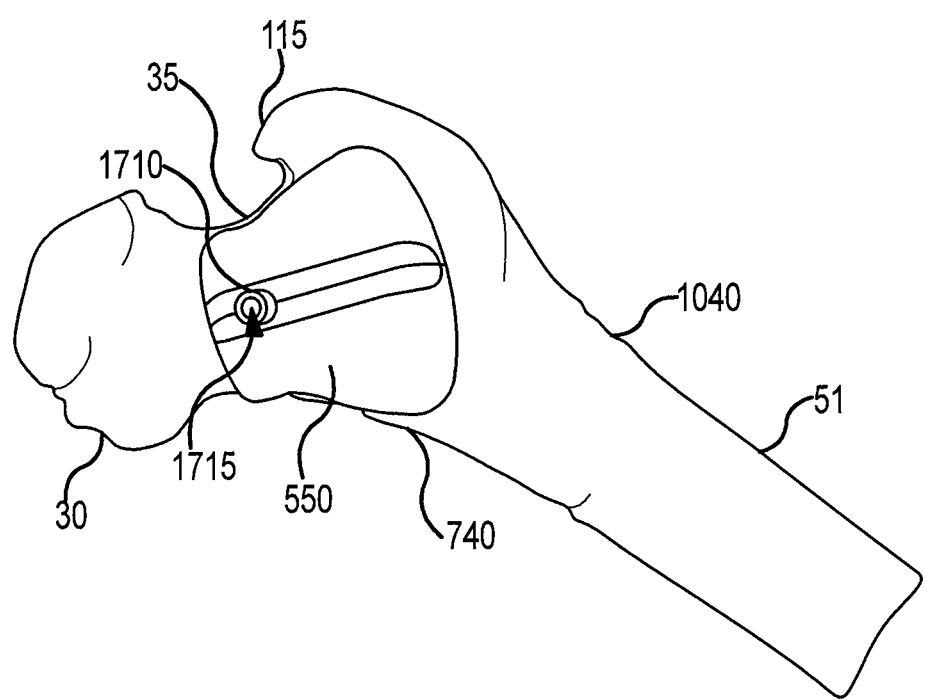
FIG. 10 is an isometric posterior view of a model of the femur of FIG. 2A, wherein the surgical guide tool blank model is shown positioned on the femur.

As can be understood from FIGS. 1B and 1C and FIG. 10, which is an isometric posterior view of the femoral model 1040 of FIG. 9C, except with the other models 701, 702, 850 hidden for clarity purposes, a 3D computer generated tool blank model 550 is generated [block 1504] and imported into the modeling space to be superpositioned with the femoral model 1040 to define the mating region 20 and saw guide 1725 in the tool blank model 550 [block 1505 and 1606]. In one embodiment for a posterior approach surgical procedure, the tool blank model 550 is positioned over the posterior surface of the femur model 1040 such that: (1) the surfaces of the femur model 1040 corresponding to the mating contact surfaces 708, 710 and non-contact surfaces 718, 720 of the femur 40, as discussed in detail below with respect to FIG. 13, are covered by the tool 5; and (2) the head 30 of the femur model 1040 is exposed.

Figure 11:
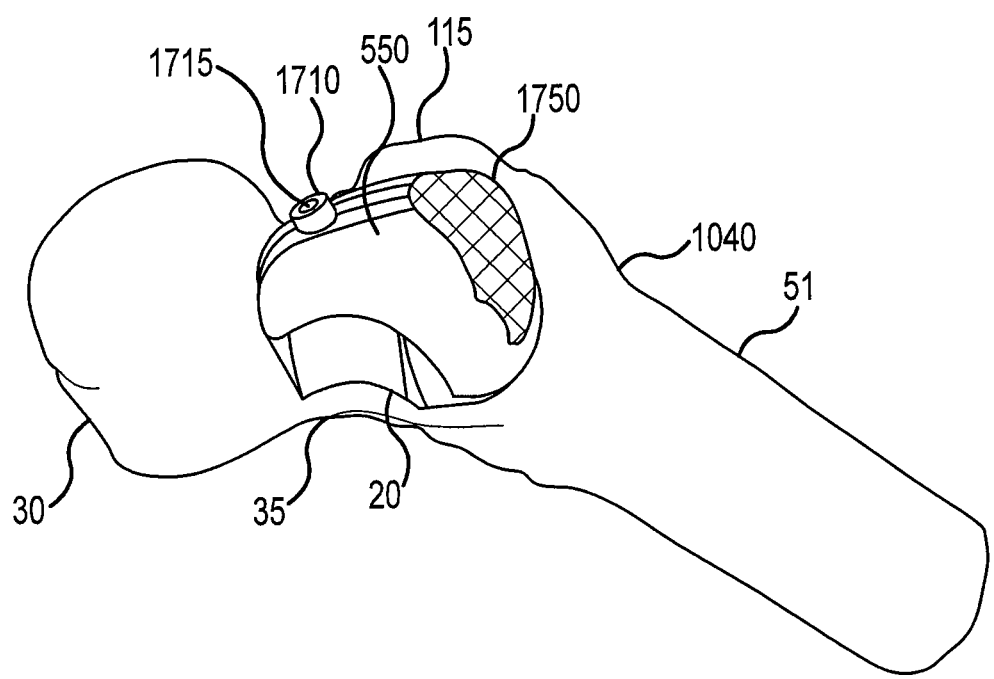
FIG. 11 is an isometric inferior-posterior view of the model of the femur and the surgical guide tool blank model, wherein the distal end of the tool model is highlighted to illustrate a portion of the tool that may be removed for proper exposure of the greater trochanter.

As shown in FIG. 11, which is a inferior-posterior isometric view of what is depicted in FIG. 10, a distal portion 1750 of the tool blank model 550 may be removed to provide a non-contacting arrangement between the resulting tool 5 and non-mating regions of the proximal femur 40, such as those regions near the greater trochanter 115.

Figure 12:
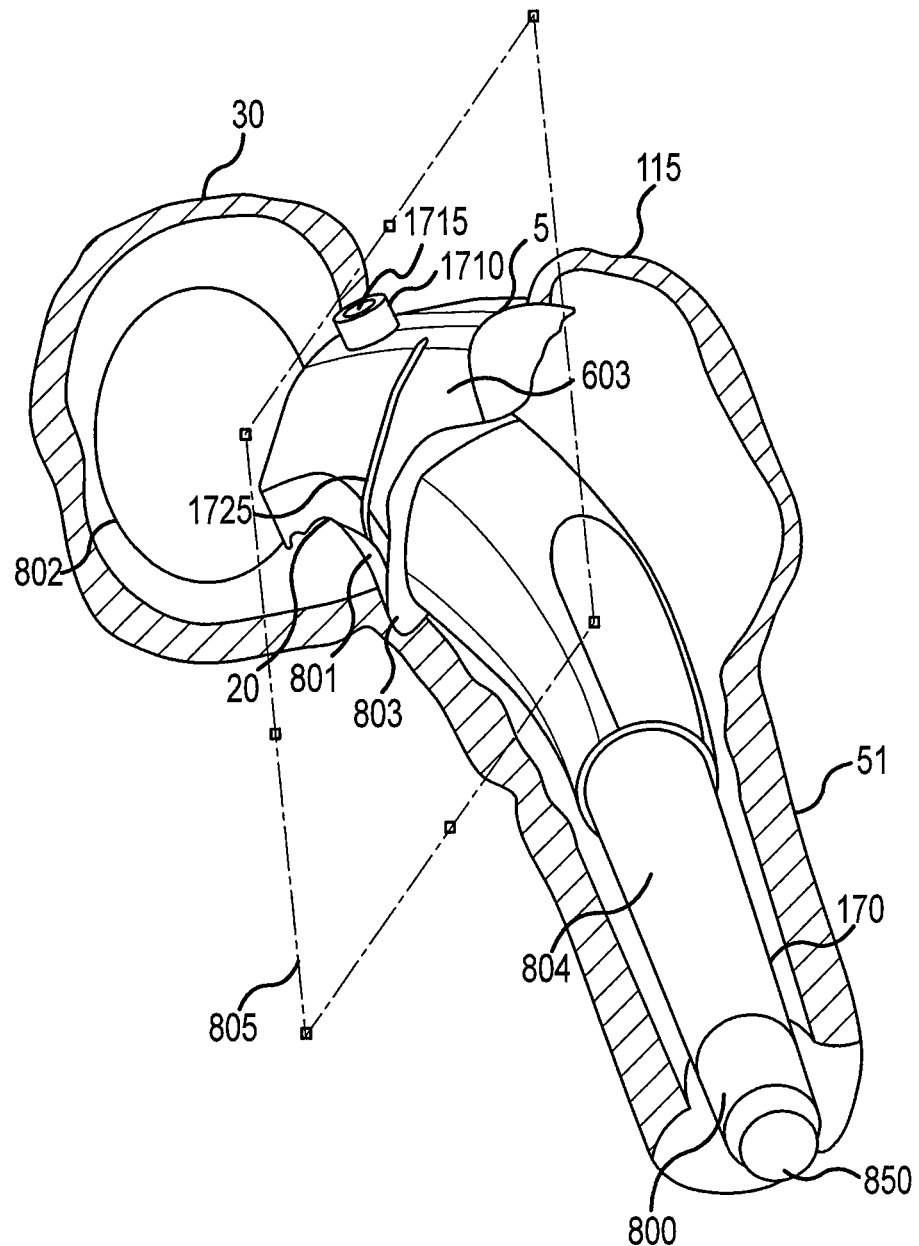
FIG. 12 is a transparent view of the femoral component model, model of the femur, and the model of the customized surgical guide tool properly superimposed relative to each other.

As can be understood from FIGS. 1B and 1C and FIG. 12, which is generally the same view as FIG. 11, except the femoral component model 850 is visible and the tool blank model 550 is now a customized tool model 603, once the tool blank model 550 is properly positioned on the femur model 1040, the tool mating region 20 and saw guide 1725 may be defined and imported into the tool blank model 550 to create the tool model 603 [block 1506 and block 1606]. Specifically, those mating contact surfaces 708a, 710a and non-contacting surfaces 718a, 720a of the tool mating region 20 that respectively correspond to the contact surfaces 708, 710 and non-contact or overestimated surfaces 718, 720 of the femur 40 of FIG. 13 are identified on the surface of the femur model 1040 and imported or otherwise used to define the contacting surfaces 708a, 710a and non-contacting surfaces 718a, 720a in the mating region of the tool blank model 550. As can be understood from FIG. 1B, in one embodiment, the contacting surfaces 708, 710 and non-contacting surfaces 718, 720 of the femur model 1040 may be identified and defined as 3D surface models 537, 539 or other types of "data" that are imported into the tool blank model 550 to create the contacting surfaces 708a, 710a and non-contacting surfaces 718a, 720a in the mating region of the tool blank model 550 [block 1506].

As can be understood from FIG. 12, since the femoral component model 850 is properly positioned in the femur model 1040 in a manner that is predicted to give a desirable surgical outcome for the hip implantation, the surface 803 of the spacer region 801 of the component model 850 may be coplanar to the resection plane 805 needed to allow the actual implanted femoral component to achieve the implant positioning that will achieve the predicted desirable surgical outcome. In other words, the spacer region surface 803 will correspond to the position and orientation of the resection plane 805 when the component model 850 is properly positioned in the femur model 1040. Thus, the position and orientation of the spacer region surface 803 may be used to define the position and orientation of the resection plane 805 and, as can be understood from FIG. 1B, a resection plane model 538 or other types of "data" may be defined and imported into the tool blank model 550 to define the saw guide 1725 in the tool blank model 550 [block 1506]. Since the location and orientation of the surface models 539, 537 and plane model 538 may be referenced relative to each other due to the femur, component and blank models 1040, 805, 550 being superimposed with each other, the position and orientation relationships are maintained in the resulting tool model 603 [block 1507]. Thus, for the resulting tool model 603 and tool 5 manufactured therefrom, the saw guide 1725 may be positioned and oriented relative to the customized mating or indexing region 20 such that, when the mating surfaces 708a, 710a of the mating region 20 matingly contact the bone surfaces 708, 710 when the tool mating region 20 matingly receives therein the region of the femur 40 having the bone surfaces 708, 710, the saw guide 1725 may be oriented over the femur neck 35 such that the saw guide 1725 corresponds with a desired resection plane 805 through the femoral neck 35 that was identified during the preoperative planning. In other words, the cavity or mating region 20 of the tool 5 conforms to the segmented CT scans or MRI scans, overestimated as necessary, of the patient's femur, and the saw guide 1725 is positioned so as to result in a preoperatively planned resection of the proximal femur when the tool mating region 20 matingly engages the proximal femur and a sawing action is guided by the saw guide 1725.

Proper alignment of the saw slot 1725 with the preoperatively planned resection plane exposes the femoral neck to provide a properly oriented surface for proper alignment of the femoral component. A properly positioned femoral component prevents or at least minimizes the chances of several undesirable complications. For example, an improperly positioned femoral component can cause a change of leg length, dislocation of the hip or perforation of the femur.

As can be understood from FIGS. 1A-1C, once the tool model 603 is defined, the tool model 603 may be used to generate automated manufacturing instructions (e.g., tool paths, etc.). The tool model 603 or automated manufacturing instructions are sent to the CNC machine 10 from the preoperative planning system 6 [block 1508], and the actual tool 5 is manufactured from an actual tool blank 50 via the CNC machine 10 [block 1608]. The finished tool 5 may be marked with patient data (e.g., name, hip identification, etc.), surgeon name, medical facility name, or other information. The tool 5 may then be sterilized, packaged and sent to the surgeon [block 1610].

During surgery, the surgeon may fit the tool appropriately on the femur and, in one embodiment, drill into the hole 1715 of the fastener feature 1710 at the top side 1755 of the tool and insert a fastening member 1716 to stabilize the tool [block 1612]. In some embodiments, the tool 5 may be held in place by the surgeon or other medical personnel. Once positioned, the surgeon may place a saw blade through the saw slot 1725 and prepare to saw through the resection plane to make at least a partial head and neck resection [block 1614]. Once the resection is at least partially complete, the tool may be discarded [block 1616]. In some embodiments, the tool 5 may remain in place until the resection is complete.

The surgeon may then further prep the resected proximal femur and then implant the femoral component 800 in a manner that replicates the preoperative planning such that the surface 803 abuts against the resection surface of the femur. As the size selection and positioning of the femoral component are determined via computer modeling during the preoperative planning process, and the tool 5 is custom configured to facilitate the preoperatively planned positioning of the femoral component, the tool 5 disclosed herein facilitates HRS that is substantially more likely to result in a positive surgical outcome for the patient as compared to conventional methods that rely on x-rays, hand measuring techniques and surgeon visual assessment. In other words, the tool 5 decreases the risks commonly associated with an improperly placed femoral component in total hip replacement surgery, such as dislocation of the hip, a change in the length of the leg or perforation of the femur.

As the surgical planning is integrated into the tool 5 prior to the time of surgery, the surgical time is substantially reduced because the surgeon simply has to cause the tool 5 to engage the proximal femur, as opposed to determining the proper location for the resection based off of visual inspection at the time of surgery. Thus, the tool 5 aids the surgeon in accurately and quickly placing the femoral component 800. In other words, the tool 5 also decreases the risks associated with the length of the surgical time, such as, infection, excessive bleeding, etc.

In one embodiment and to a greater or lesser extent, the above-described POP procedure is a manual process, wherein computer generated 3D models 701, 702, 1040, 850 are manually manipulated relative to each other by a person sitting in front of a computer 6 and visually observing the 3D models 701, 702, 1040, 850 on the computer screen 9 and manipulating the 3D models 701, 702, 1040, 850 via the computer controls 11. In other embodiments and to a greater or lesser extent, the POP process is generally or completely automated. For example, a computer program may manipulate computer generated 3D models 701, 702, 1040, 850 relative to each other to preoperatively plan the tool 5. In some embodiments, the above-described POP process may have portions that are generally manual while other portions that are generally automated.

VI. Candidate Contact and Non-Contact Surfaces of Proximal Femur

As described in detail above, the mating region 20 of the tool 5 may be customized based on a patient's individual bone shape. The tool 5 may be machined, molded or otherwise formed from the non-customized state as illustrated in FIGS. 2B-2E to a customized state as indicated in FIGS. 2F-2H, based on a patient's individual bone scan, for example an MRI scan or CT-scan. For example, the bone scan data may be utilized to generate a 3D computer generated model 1040 of the patient's proximal femur 40. A 3D computer generated model 550 of the blank of the tool 5, the 3D femur model 1040, and 3D computer generated models of the implant component 850, the sphere 701, and the rod 702 may be superimposed and aligned as described above to preoperatively plan the patient specific tool 5. That is, through the information received from the MRI scan or CT-scan and the computer modeling, the tool 5 may be customized at the mating region 20 such that the tool 5 will have mating or indexing surfaces 708a, 710a of the mating region 20 that generally conform to the predetermined specific surface geometry of the patient's own proximal femur 40. In some embodiments, the predetermined specific geometry will be that of surfaces 708, 710 discussed with respect to FIG. 13, which is a posterior medial view of the proximal femur 40 of FIG. 2A showing the surfaces 708, 710 of the femur 40 that are mated with the index surfaces 708a, 710a of the tool mating region 20 and the surfaces 718, 720 that correspond to over-estimated or non-contacting surfaces 718a, 720a of the tool mating region 20.

In one embodiment, the femur mating region depicted in FIG. 13 may be applicable to a posterior approach to help with stable positioning of the tool 5 on the femur 40. As shown in FIG. 13, a first mating surface 708 covers portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 210. The inferior boundary of surface 708 may terminate approximately 5 mm superior to the inferior border between the posterior and anterior surfaces of the neck 35, or may extend up to approximately 5 mm anterior past this border. The superior boundary of mating surface 708 may extend approximately 0 mm to approximately 5 mm posterior to the superior junction between the posterior surface and the anterior surface of the neck 35. A second mating surface 710 may be a narrow band measuring between approximately 0.5 mm and approximately 12 mm medial-lateral. The second mating surface 710 may follow along the intertrochanteric crest 116. Mating surface 710 may begin approximately 0 mm to approximately 12 mm superior to the lesser trochanter 740 and may extend approximately 0 mm to approximately 18 mm inferior to the most superior tip 215 of the posterior surface of the greater trochanter 115. These mating surfaces 708, 710 of the femur 40 may be used to define the mating contact surfaces 708a, 710a of the tool mating region 20 (see FIG. 2G) such that the tool contact surfaces 708a, 710a may matingly contact the femur surfaces 708, 710 when the tool mating region 20 mating receives or engages the femur 40 as depicted in FIG. 2H.

The non-mating surfaces 718, 720 of the femur 40, which are spanned in a spaced-apart or non-contacting arrangement by corresponding non-contacting surfaces 718a, 720a of the tool mating region 20, as depicted in FIG. 2H, are also depicted in FIG. 13. A first non-mating surface 718 may include portions of the posterior greater trochanter 115 and extend superior-inferior adjacent the intertrochanteric crest 116. The medial boundary of the first non-mating surface 718 may be the second mating surface 710, and may extend medial-lateral approximately 0 mm to approximately 12 mm. The second non-mating surface 20 may span portions of the trochanteric fossa 210, and may have a medial boundary that is the first mating surface 708 and a lateral boundary that is the second mating surface 710, and a medial-lateral width that may vary between approximately 0 mm and approximately 20 mm. Both the first non-mating surface 718 and the second non-mating surface 720 may have inferior-superior dimensions similar to the first mating surface 708 and the second mating surface 710.

As discussed in detail above, during segmentation, contour line portions corresponding to non-mating surfaces 718, 720 and osteophytes may be overestimated (e.g., moved outward from the interior of the bone and smoothed) such that portions of the tool mating region 20 defined according to those overestimated contour line portions are over-machined, ensuring that little or no contact occurs between the resulting non-mating surfaces 718a, 720a of the tool mating region 20 (see FIG. 2G) and the corresponding non-mating surfaces 718, 720 of the bone when the tool mating region 20 matingly receives the region of the femur 40 having the non-mating surfaces 718, 720, as shown in FIG. 2H.

As just discussed with respect to FIG. 13, in one embodiment, the femur 40 may include contact surfaces 708, 710 and non-contact surfaces 718, 720 such that a tool 5 configured for a posterior approach may have a mating region 20 configured to have corresponding mating contact surfaces 708a, 710a and non-contacting surfaces 718a, 720a, as indicated in FIGS. 2G and 2H. In other embodiments, the tool mating region 20 may be such that the mating contact and non-contact surfaces of the tool mating region 20 are configured to correspond to mating and non-contact surfaces of other regions of the femur 40 as described below with respect to FIGS. 14A-14B, 15 and 16A-16B.

Figure 14A:
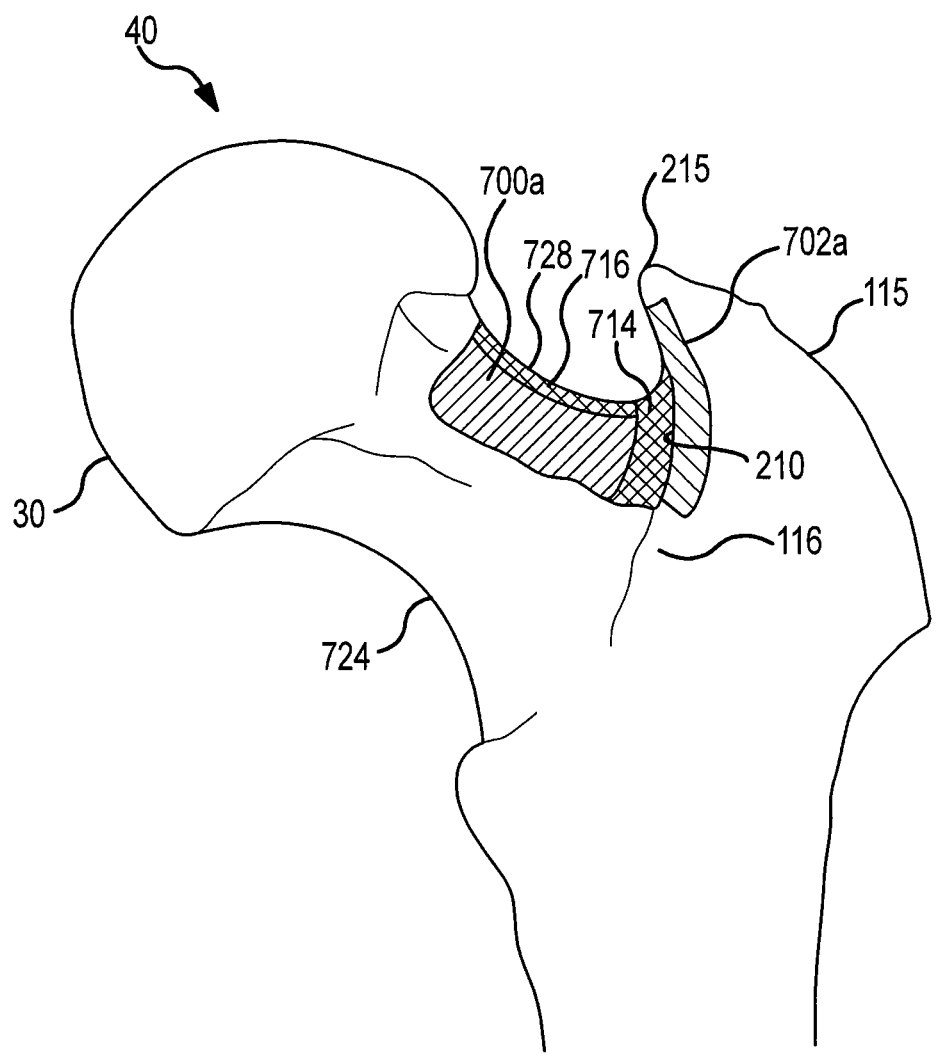
FIGS. 14A-14B are, respectively, posterior and anterior views of the proximal femur, wherein the mating region of the femur may be appropriate for a posterior or anteriorlateral surgical approach.
Figure 14B:
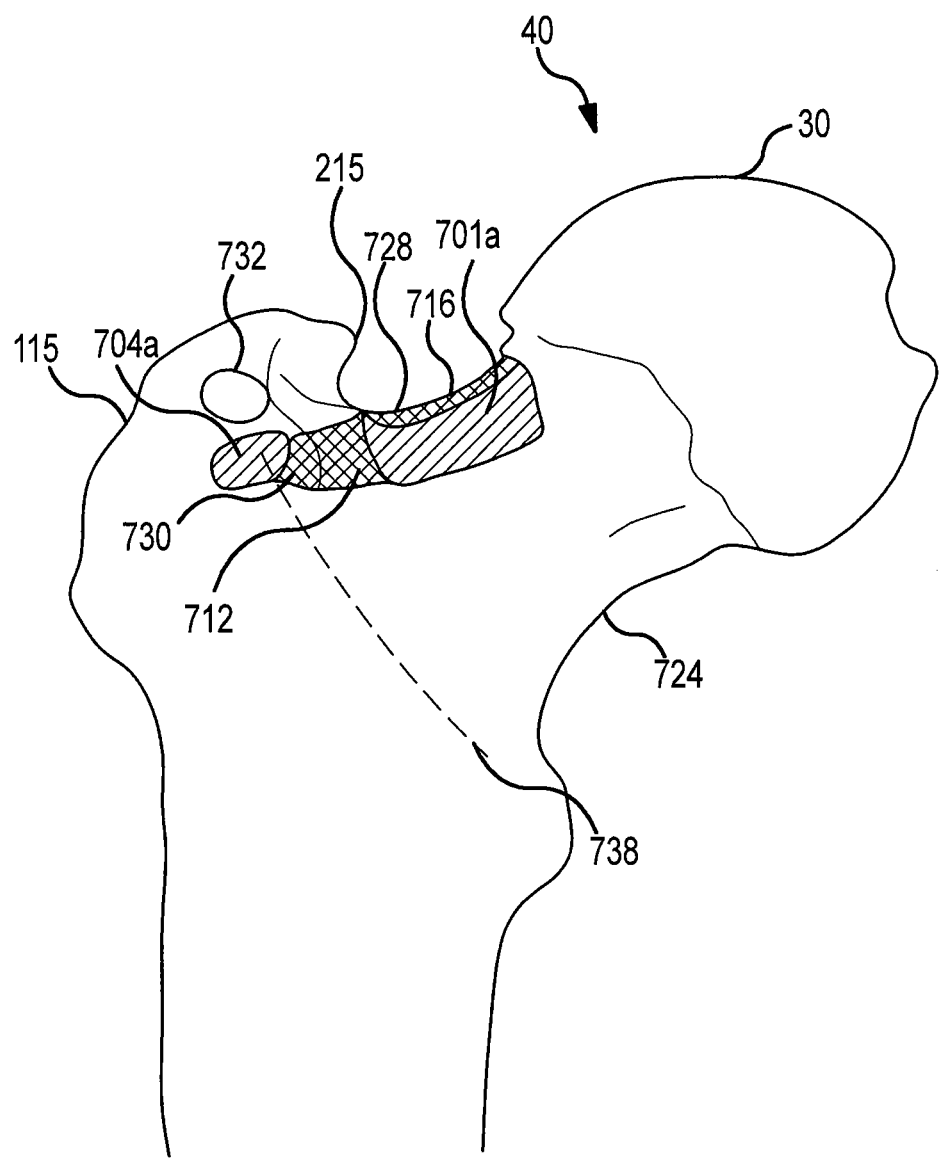

As shown in FIGS. 14A-14B, which are, respectively, posterior and anterior views of the proximal femur 40, the mating region of the femur 40 may be appropriate for a posterior or anteriorlateral surgical approach. For example, the mating region of the femur 40 may include mating surfaces 700a, 701a, 702a, 704a. As can be understood from FIG. 2I, which is a view similar to FIG. 2G, except of a tool mating region 20 configured to matingly engage the mating surfaces 700a, 701a, 702a, 704a depicted in FIGS. 14A-14B, the mating surfaces 700a, 701a, 702a, 704a of the femur 40 may be matingly contacted by corresponding mating or index contact surfaces 700b, 701b, 702b, 704b of the tool mating region 20 to help stabilize the positioning of the tool 5 on the femur 40. In other words, like the tool mating region 20 depicted in FIG. 2G is configured to matingly engage the mating surfaces of the femur 40 depicted in FIG. 13, the tool mating region 20 depicted in FIG. 2I is configured to matingly engage the mating surfaces of the femur 40 depicted in FIGS. 14A-14B.

As indicated in FIGS. 14A-14B, a first mating surface 700a includes portions of the posterior region 724 of the neck 35, having a medial starting point between approximately 1 mm and approximately 5 mm after the cartilage covering the femoral head 30 terminates laterally and extends laterally between approximately 15 mm and approximately 35 mm to or towards the trochanteric fossa 210. The inferior border of the first mating surface 700a begins approximately midway superiorly-inferiorly along the intertrochanteric crest 116, and follows the long axis of the neck 35. The superior border of the first mating surface 700a is between approximately 1 mm and approximately 3 mm below the superior junction 728 between the posterior and anterior surfaces of the neck 35. A second mating surface 701a has approximately the same medial-lateral width as section 700a, but may terminate before the tubercle 730 of the femur 40. The superior border of the second mating surface 701a is approximately 1 mm to approximately 3 mm below the superior junction 728 between the posterior and anterior surfaces of the neck 35. The inferior-superior distance of second mating surface 701a is between 5 and 10 mm. A third mating surface 702a is a narrow band, measuring generally medial-lateral between approximately 0.5 mm and approximately 8 mm, that follows along the intertrochanteric crest 116. Mating surface 702a begins approximately midway superior-inferior along the intertrochanteric crest 116 and may extend any length greater than approximately 5 mm to or towards the most superior tip 215 of the posterior surface of the greater trochanter 115. A fourth mating surface 704a lies on the anterior greater trochanter 115, lateral to the tubercle 730 of the femur 40, and inferior to the origin of the obturator internus 732. The medial-lateral distance of mating surface 704a measures between approximately 3 mm to approximately 14 mm, and its inferior-superior distance measures between approximately 3 mm to approximately 10 mm.

Figure 2I:
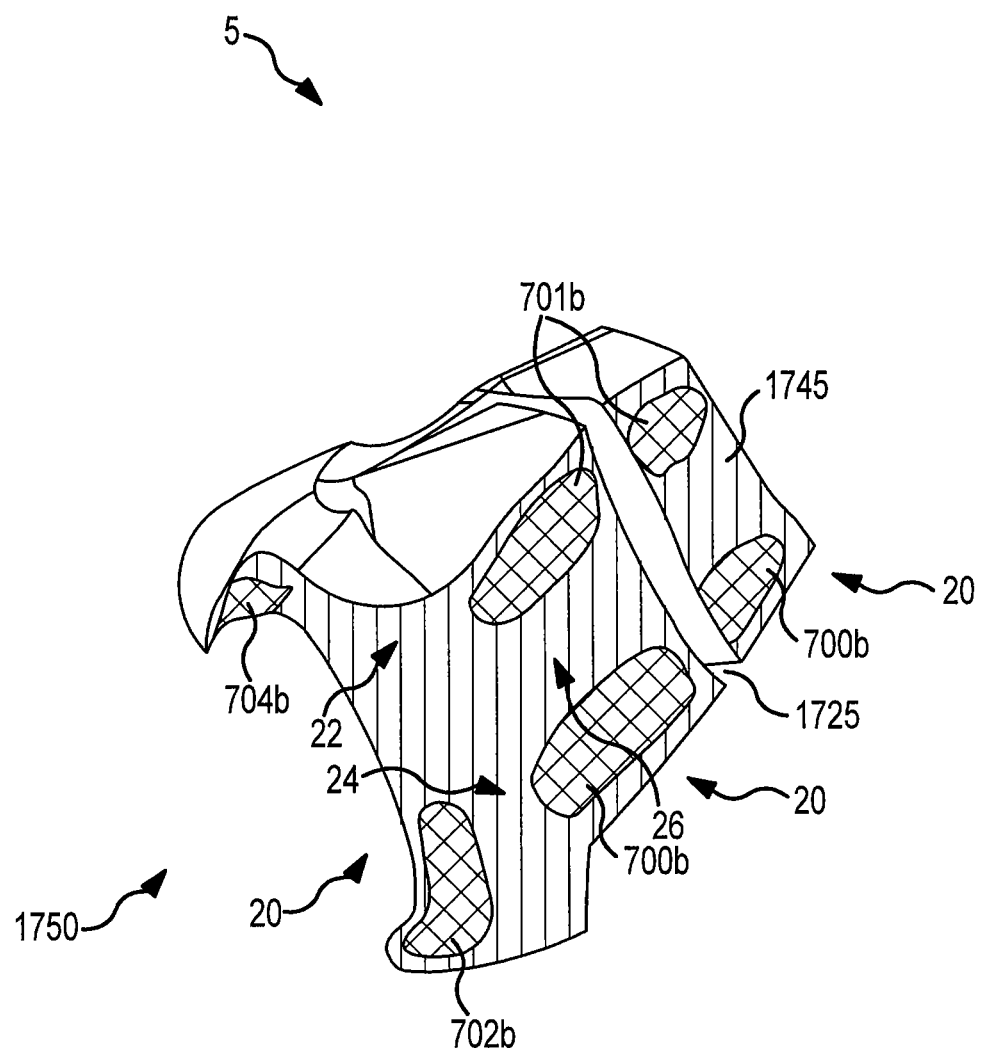
FIG. 2I is a view similar to FIG. 2G, except of a tool with a mating region configured to matingly engage the mating region of the femur depicted in FIGS. 14A-14B.

As indicated in FIGS. 14A-14B, mating surfaces 700a, 701a, 702a, 704a may be separated by non-mating surfaces 712, 714, 716 that are spanned by and correspond respectively with non-contacting surfaces 22, 24, 26 of the mating region 20 of the tool 5 (see FIG. 2I). A first non-mating surface 712 may include portions of the tubercle 730 of the femur 40. A second non-mating surface 714 may span portions of the trochanteric fossa 210. A third non-mating surface 716 may contain the superior junction 728 between the posterior and anterior surfaces of the neck 35, and may be between approximately 1 mm to approximately 5 mm anterior-posterior. In a manner similar to that described above with respect to the non-contact surfaces 718a, 720a of the tool mating region 20 depicted in FIGS. 2G-2H, during segmentation, contour line portions corresponding to non-mating surfaces 712, 714, 716 may be overestimated (e.g., moved outward from the interior of the bone and smoothed) such that portions of the tool mating region 20 defined according to those overestimated contour line portions are over-machined, ensuring that little or no contact occurs between the resulting non-mating surfaces 22, 24, 26 of the tool mating region 20 (see FIG. 2I) and the corresponding non-mating surfaces 712, 714, 716 of the femur 40 when the tool mating region 20 matingly receives the region of the bone having the non-mating surfaces 712, 714, 716.

Figure 2J:
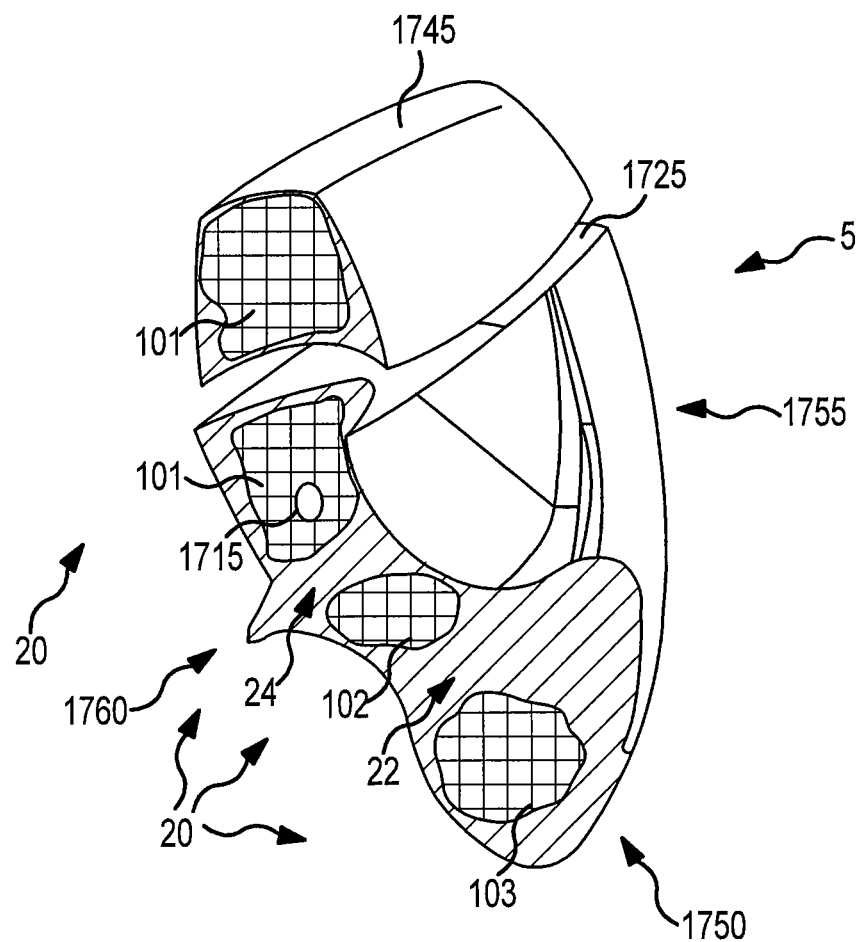
FIG. 2J is the same view as 2G, except of a tool with a mating region configured to matingly engage the mating region of the femur depicted in FIG. 15.
Figure 15:
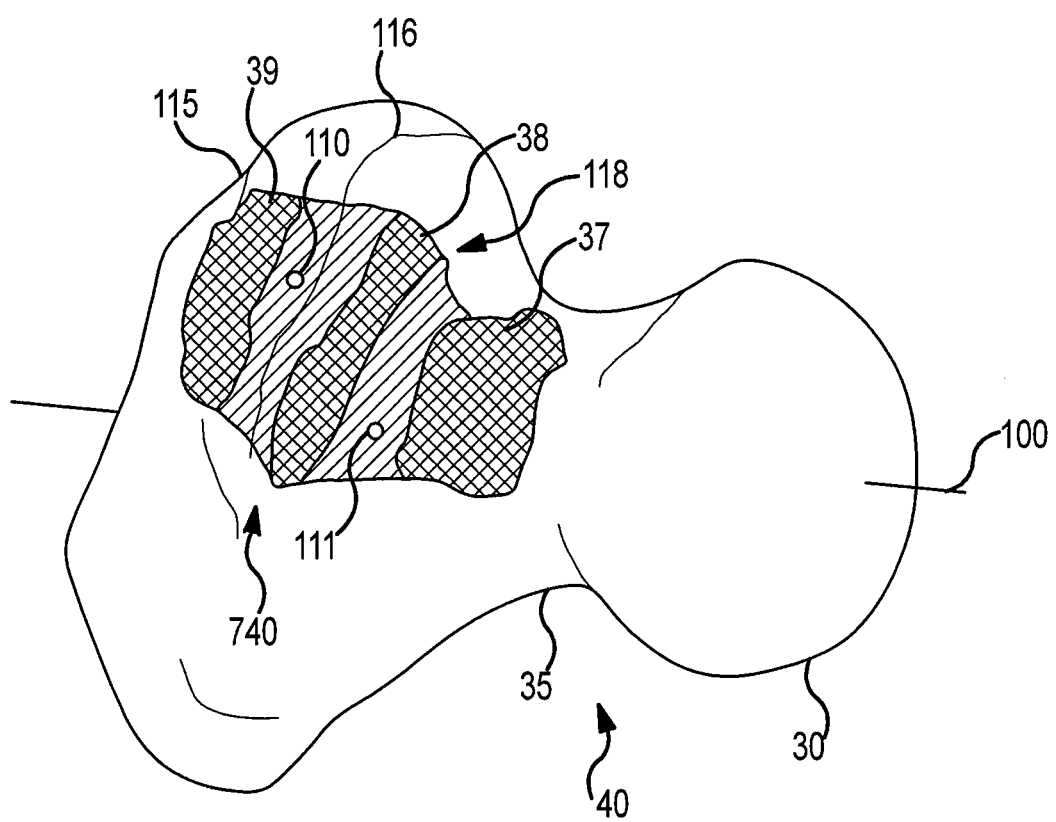
FIG. 15 is an isometric posterior view of the proximal femur and illustrates yet another mating region of the femur that may be used to define the mating region of another embodiment of the tool configured for a posterior surgical approach.

FIG. 15, which is an isometric posterior view of the proximal femur 40, illustrates yet another mating region of the femur 40 that may be used to define the mating region 20 of another embodiment of the tool 5. As can be understood from FIG. 15 and FIG. 2J, which is the same view as 2G, except of a tool 5 with a mating region 20 configured to matingly engage the mating region of the femur 40 depicted in FIG. 15 instead of the mating region of the femur 40 depicted in FIG. 13, the tool mating region 20 may be adapted to receive therein and mate with surfaces of the proximal femur 40, such as, for example, the posterior region 37 of the neck 35, a medial posterior surface 38 of the greater trochanter 115 between the intertrochanteric crest 116 and trochanteric fossa 118, and a region 39 that is part of the lateral posterior greater trochanter 115 and the lateral posterior body of the femur bordering the lateral side of the intertrochanteric crest 116. More specifically, the mating surface 37 may cover portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 118. Region 38 may be a band, extending from the lesser trochanter 740 to the anterior surface of the femur, and ranging in width from between approximately 0 mm to approximately 14 mm. The medial border of region 38 is the trochanteric fossa 118 and the lateral border is approximately the intertrochanteric crest 116. Region 39 begins medially at approximately the crest 116, and may extend from 0 mm to approximately the edge of the posterior surface of the femur 40. The inferior/superior length of region 39 may be 0 mm, or may extend from the lesser trochanter 740 to the superior border of the posterior surface of the femur 40.

The surfaces 37, 38, 39, which are to be mated or indexed by the tool index surfaces 101, 102, 103 of the mating region 20 of the tool 5, may be separated by areas of non-mating surfaces 110, 111 that are spanned by overestimated or non-contacting surfaces 22, 24 of the mating region 20 of the tool 5. The non-contacting surfaces 22, 24 of the mating region 20 of the tool 5 do not contact the corresponding non-mating surfaces 110, 111 of the femur 40 and may be generated via an over-estimating process during image segmentation. The non-mating surfaces 110, 111 of the proximal femur 40 may be portions 111 of the trochanteric fossa 118 (i.e., the depression between the greater trochanter and the femur neck) and portions 110 of the intertrochanteric crest 116. More specifically, the non-mating surface or portion 111 may span portions of the trochanteric fossa 118, and may have a medial boundary that is the mating surface 37 and a lateral boundary that is the mating surface 38, and a medial-lateral width that may vary between approximately 0 mm and approximately 20 mm. Non-mating surface or portion 110 may be a band including the intertrochanteric crest 116, and may extend from the lesser trochanter 740 to the most superior point of the greater trochanter 115. The medial-lateral width of the surface 110 may be from approximately 0 mm to approximately 12 mm. Generally, any surface of mating region 20 that is outside of tool mating surfaces 101, 102, 103 (which correspond to femur mating surfaces 37, 38, 39, respectively) may be tool non-contacting surfaces 22, 24, which correspond, respectively to femur non-contacting surfaces 110, 111.

As can be understood from FIG. 15, the tool may be placed on the femur 40 such that the mating region 20 of the tool 5 covers and matingly receives the femur area encompassing the mating surfaces 37, 38, 39 and non-mating surfaces 110, 111 of the proximal femur 40. As discussed above, non-mating regions 110, 111, including portions of the trochanteric fossa 118 (the depression between the greater trochanter and the neck of femur) and the intertrochanteric crest 116, are not easily estimated due to drastic changes in surface geometry, and corresponding non-mating surfaces 22, 24 of the mating region 20 of the tool 5 do not contact these surfaces 110, 111 when the region of the femur that includes the femur mating surfaces 37, 38, 39 and non-mating surfaces 22, 24 are matingly received by the mating region 20 of the tool 5.

Figure 16A:
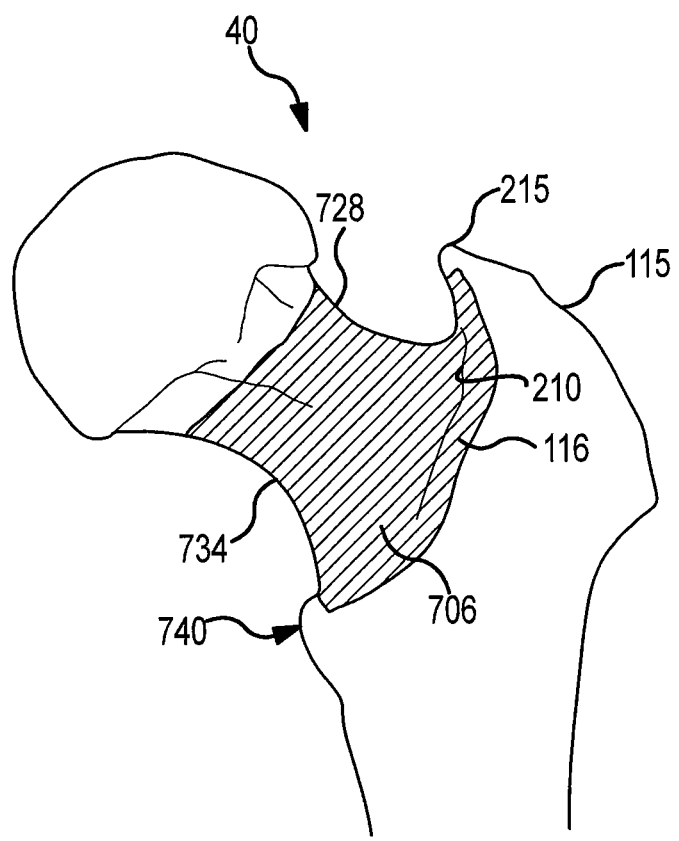
FIGS. 16A-16B are, respectively, posterior and anterior views of the proximal femur, wherein the mating region of the femur may be appropriate for a posterior or anteriorlateral surgical approach.
Figure 16B:
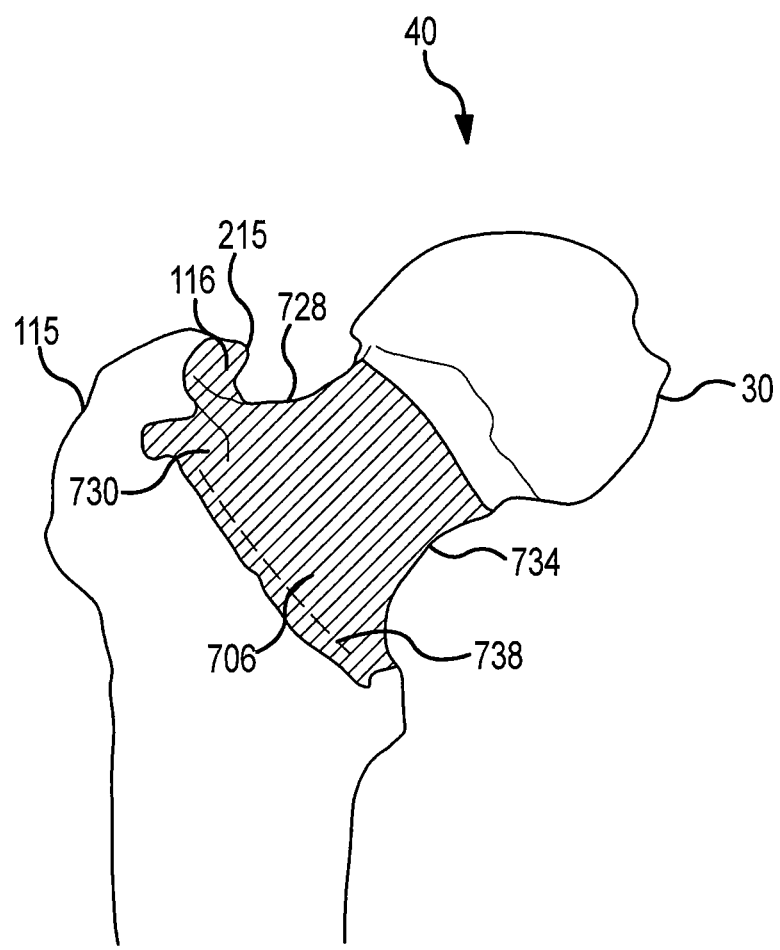

In other embodiments, as shown in FIGS. 16A-16B, the mating region of the femur 40 may be configured for use with any surgical approach, and, in a manner similar to that discussed above with respect to FIGS. 2G-2H and 13 and FIGS. 2I and 14A-14B, the tool mating region 20 may be configured to matingly engage the mating region of the femur 40 as depicted in FIGS. 16A-16B. As illustrated in FIGS. 16A-16B, a first mating surface 706 of the femur 40 may include the entire or any portion of the circumferential surface 734 of the neck 35. On the posterior surface, the mating surface 706 may start medially between approximately 1 mm and approximately 5 mm after the cartilage covering the head 30 of the femur 40 terminates laterally and extend laterally up to approximately 8 mm past the intertrochanteric crest 116, extending along the intertrochanteric crest 116 from the lesser trochanter 740 to or towards the tip 215 of the greater trochanter 115. On the anterior surface, the mating surface 706 may start medially between approximately 1 mm and approximately 5 mm after the cartilage covering the head 30 of the femur 40 terminates laterally and extend laterally up to approximately 8 mm laterally past the intertrochanteric line 738. The surface 706 may also contain the medial surface of the greater trochanter 115. As discussed above, portions within the mating surface 706 may be overestimated if geometry is too erratic for the surface to be accurately captured with the CT scan. Some such areas may include the trochanteric fossa 210, the superior junction 728 between the posterior and anterior surfaces of the neck 35, and the tubercle 730.

As can be understood from the preceding discussion regarding FIGS. 13-16B, the configuration of the mating region 20 of the tool 5 may be determined from and correspond to the specific surface geometry or topography of the surface of the femur 40 that corresponds to the surgical approach for which the tool 5 is being designed. Thus, in some embodiments, the tool mating region 20 may be configured to have the contact and non-contact surfaces that correspond to at least some, if not all, of the contact and non-contact surfaces of the femur mating region discussed above with respect to FIG. 13. In other embodiments, the tool mating region 20 may be configured to have the contact and non-contact surfaces that correspond to at least some, if not all, of the contact and non-contact surfaces of the femur mating region discussed above with respect to FIGS. 14A-14B. In yet other embodiments, the tool mating region 20 may be configured to have the contact and non-contact surfaces that correspond to at least some, if not all, of the contact and non-contact surfaces of the femur mating region discussed above with respect to FIG. 15. In still other embodiments, the tool mating region 20 may be configured to have the contact and non-contact surfaces that correspond to at least some, if not all, of the contact and non-contact surfaces of the femur mating region discussed above with respect to FIGS. 16A-16B. Thus, regardless of the surgical approach used and the mating region of the femur 40 encountered, the tool mating region 20 may be based off of the medical imaging scans take of the femur 40 and preoperatively planned via 3D computer generated models to have a customized engagement with the femur 40 when applied to the femur to guide a resection in a THR. The arrangement between the customized mating region 20 of the tool 5 and the saw guide 1725 may be such that when the mating region 20 matingly receives the mating region of the femur 40, the saw guide 1725 may cause a resection procedure guided by the guide 1725 to create a preoperatively planned resection of the femur 40.

While the above disclosed embodiments of a arthroplasty tool 5 or surgical guide tool 5 are described in the context of a tool 5 for use in a total hip replacement procedure, the features, methods of determining proper placement of the prosthetic device and the mating surfaces and the generation thereof disclosed herein may be equally useful and applicable for use in total arthroplasty procedures in other joint contexts.

Thus, the disclosure provided herein should be considered as encompassing tools and the generation thereof for any total arthroplasty procedures.

Although the present invention has been described with reference to preferred embodiments, persons skilled in the art will recognize that changes may be made in form and detail without departing from the spirit and scope of the invention.

What is claimed is:

1. A surgical guide tool for use in the preparation of a proximal portion of a femur for the implantation of a total hip replacement prosthetic implant, the implant including a feature configured to abut against a resection surface of the proximal femur when the implant is fully implanted in the proximal femur in a manner that generally replicates a preoperatively planned implantation for the implant, the tool comprising: a mating region including a customized surface contour that is generally a negative of the proximal portion of the femur, the surface contour of the mating region being configured to matingly contact the proximal portion in a generally matching or interdigitating manner when the proximal portion is matingly received by the mating region and a saw guide, wherein, when the mating region matingly contacts the proximal portion, the saw guide is aligned with a resection plane generally corresponding to the resection surface.

2. The tool of claim 1, wherein the saw guide includes at least one planar surface.

3. The tool of claim 2, wherein the at least one planar surface forms a saw slot.

4. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a superior-posterior region of the neck, the at least a portion of a superior-posterior region of the neck starting between approximately 1 mm and approximately 5 mm after a cartilage covering the head terminates distally and extending between approximately 15 mm and approximately 35 mm towards a trochanteric fossa.

5. The tool of claim 4, wherein the saw guide includes at least one planar surface.

6. The tool of claim 4, wherein the at least a portion of a superior-posterior region of the neck has an inferior border that begins approximately midway along an intertrochanteric crest and follows along the axis of the neck.

7. The tool of claim 6, wherein the at least a portion of a superior-posterior region of the neck has a superior border between approximately 1 mm and approximately 3 mm below a junction between superior and anterior surfaces of the neck.

8. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a superior-posterior region of the neck, the at least a portion of a superior-posterior region of the neck including a narrow band that follows along an intertrochanteric crest and has a medial-lateral width of between approximately 0.5 mm and approximately 8 mm.

9. The tool of claim 8, wherein the saw guide includes at least one planar surface.

10. The tool of claim 8, wherein the at least a portion of a superior-posterior region of the neck begins approximately midway along the intertrochanteric crest and extends at least approximately 5 mm towards a most superior tip of a posterior surface of a greater trochanter.

11. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a superior-anterior region of the neck, the at least a portion of a superior-anterior region of the neck starting between approximately 1 mm and approximately 5 mm after a cartilage covering the head terminates distally and extending between approximately 15 mm and approximately 35 mm to terminate before a tubercle.

12. The tool of claim 11, wherein the saw guide includes at least one planar surface.

13. The tool of claim 11, wherein the at least a portion of a superior-anterior region of the neck has a superior border approximately 1 mm to approximately 3 mm below a junction between superior and anterior surfaces of the neck.

14. The tool of claim 13, wherein the at least a portion of a superior-anterior region of the neck has an inferior border that is between approximately 5 mm and approximately 10 mm from the superior boarder.

15. The tool of claim 11, wherein the at least a portion of a superior-anterior region of the neck lies on an anterior greater trochanter, distal to a tubercle, and inferior to an origin of an obturator internus.

16. The tool of claim 15, wherein the at least a portion of a superior-anterior region has a medial-lateral distance that measures between approximately 3 mm to approximately 14 mm.

17. The tool of claim 15, wherein the at least a portion of a superior-anterior region has an inferior-superior distance that measures between approximately 3 mm to approximately 10 mm.

18. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a superior-posterior region of the neck and at least a portion of a superior-anterior region of the neck, but does not include a junction between the superior-posterior and superior-anterior regions of the neck.

19. The tool of claim 18, wherein the saw guide includes at least one planar surface.

20. The tool of claim 18, wherein the at least a portion of the superior-posterior region of the neck includes an area that extends along the intertrochanteric chest, but does not include an area that spans portions of a trochanteric fossa.

21. The tool of claim 20, wherein the at least a portion of a superior-anterior region of the neck lies on an anterior greater trochanter, distal to a tubercle, and inferior to an origin of an obturator internus, but does not include portions of the tubercle.

22. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a posterior region of the neck, the at least a portion of the posterior region of the neck including an area that extends towards a trochanteric fossa between approximately 15 mm and approximately 35 mm from a first point being between approximately 1 mm and approximately 5 mm distal of a distal termination of a cartilage covering the head.

23. The tool of claim 22, wherein the saw guide includes at least one planar surface.

24. The tool of claim 22, wherein the at least a portion of a posterior region of the neck has an inferior border that terminates up to approximately 5 mm superior to a border between posterior and inferior surfaces of the neck.

25. The tool of claim 22, wherein the at least a portion of a posterior region of the neck has a superior border that terminates approximately 0 mm to approximately 5 mm posterior of a border between posterior and anterior surfaces of the neck.

26. The tool of claim 22, wherein the at least a portion of a posterior region of the neck extends along an intertrochanteric crest from a lesser trochanter to a point near a tip of a greater trochanter.

27. The tool of claim 26, wherein the at least a portion of a posterior region of the neck does not include at least one of a portion of the trochanteric fossa and a portion of posterior region of the greater trochanter.

28. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a posterior region of the neck, the at least a portion of the posterior region of the neck including an area that includes a narrow band measuring between approximately 0.5 mm and approximately 12 mm and following along an intertrochanteric crest.

29. The tool of claim 28, wherein the saw guide includes at least one planar surface.

30. The tool of claim 28, wherein the narrow band begins approximately 0 mm to approximately 12 mm superior to a lesser trochanter.

31. The tool of claim 30, wherein the narrow band extends approximately 0 mm to approximately 18 mm inferior to a most superior tip of a posterior surface of a greater trochanter.

32. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a posterior region of the neck, the at least a portion of the posterior region of the neck including an area that extends towards a trochanteric fossa from a first point being between approximately 1 mm and approximately 5 mm distal of a distal termination of a cartilage covering the head, but does not include an area spanning portions of the trochanteric fossa.

33. The tool of claim 32, wherein the saw guide includes at least one planar surface.

34. The tool of claim 32, wherein the area spanning portions of the trochanteric fossa has a width generally transverse to a femoral longitudinal axis of between approximately 0 mm and approximately 20 mm.

35. The tool of claim 32, wherein the at least a portion of the posterior region of the neck further includes an area that includes a band following along an intertrochanteric crest, but does not include portions of a posterior greater trochanter.

36. The tool of claim 32, wherein the portions of the posterior greater trochanter has a distally extending dimension of between approximately 0 mm and approximately 12 mm.

37. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of an anterior region of the neck, the at least a portion of an anterior region of the neck extending up to approximately 8 mm laterally past an intertrochanteric line.

38. The tool of claim 37, wherein the saw guide includes at least one planar surface.

39. The tool of claim 37, wherein the surface region includes a medial surface of a greater trochanter.

40. A surgical guide tool for use in total hip replacement surgery on a proximal portion of a femur having a head, a neck extending distally from the head, and a surface region distal the head, the tool comprising: a body including a saw guide and a mating region, the mating region including a customized surface contour that is generally a negative of the surface region of the proximal portion of the femur, the surface contour of the mating region being configured to matingly contact the surface region in a generally matching or interdigitating manner when the surface region is matingly received by the mating region, the saw guide and mating region being positioned relative to each other so the saw guide is positioned to guide a resection that generally corresponds to a preoperatively planned resection plane when the mating region matingly contacts the surface region, the surface region including at least a portion of a lateral posterior greater trochanter.

41. The tool of claim 40, wherein the saw guide includes at least one planar surface.

42. The tool of claim 40, wherein the surface region further includes at least a portion of a medial posterior greater trochanter.

43. The tool of claim 42, wherein the surface region does not include at least a portion of an intertrochanteric crest.

44. The tool of claim 40, wherein the surface region further includes at least a portion of a posterior region of the neck.

45. The tool of claim 44, wherein the surface region does not include at least a portion of a trochanteric fossa.

46. The tool of claim 40, wherein the surface region further includes at least a portion of a medial posterior greater trochanter and at least a portion of a posterior region of the neck, and wherein the surface region does not include at least a portion of an intertrochanteric crest and does not include at least a portion of an trochanteric fossa.

47. A surgical guide tool for use in total hip replacement surgery on a proximal portion of a femur, the tool comprising: a mating region including a customized surface contour that is generally a negative of a surface region of the proximal portion of the femur, the surface contour of the mating region being configured to matingly contact the surface region in a generally matching or interdigitating manner when the surface region is matingly received by the mating region and a saw guide, wherein, when the mating region matingly contacts the surface region of the proximal portion, the saw guide is generally aligned with a preoperatively planned resection plane.

48. The tool of claim 47, wherein the saw guide includes at least one planar surface.

49. The tool of claim 48, wherein the at least one planar surface forms a saw slot.

50. The tool of claim 47, wherein the mating region includes contact surfaces and non-contact surfaces, wherein, when the mating region matingly contacts the proximal portion, the contact surfaces matingly contact surfaces of the proximal portion opposing the contact surfaces, and the non-contact surfaces are spaced apart from surfaces of the proximal portion opposing the non-contact surfaces.

51. The tool of claim 50, wherein the non-contact surfaces are a result of an overestimation process.

\* \* \* \* \*